United States Patent
Cros et al.

(10) Patent No.: US 10,583,114 B2
(45) Date of Patent: Mar. 10, 2020

(54) COMPOSITIONS COMPRISING UROLITHINS AND USES THEREOF FOR THE STIMULATION OF INSULIN SECRETION

(71) Applicants: Centre National de la Recherche Scientifique (CNRS), Paris (FR); Universite de Montpellier, Montpellier (FR); University of Parma, Parma (IT); Ecole Nationale Superieure de Chimie, Montpellier (FR)

(72) Inventors: Gerard Cros, Montpellier (FR); Alan Crozier, Scotland (GB); Margherita Dall'asta, Parma (IT); Daniele Del Rio, Parma (IT); Richard Magous, Lunel (FR); Catherine Oiry, Pignan (FR)

(73) Assignees: Centre National de la Recherche Scientifique (CNRS), Paris (FR); Universite de Montpellier, Montpellier (FR); University of Parma, Parma (IT); Ecole Nationale Superieure de Chimie, Montpellier (FR); Centre National de la Recherche Scientifique, Paris (FR); Universite de Montpellier, Montpellier (FR)

( * ) Notice: Subject to any disclaimer, the term of this patent is extended or adjusted under 35 U.S.C. 154(b) by 0 days.

(21) Appl. No.: 15/029,384

(22) PCT Filed: Oct. 15, 2014

(86) PCT No.: PCT/EP2014/072152
§ 371 (c)(1),
(2) Date: Apr. 14, 2016

(87) PCT Pub. No.: WO2015/055736
PCT Pub. Date: Apr. 23, 2015

(65) Prior Publication Data
US 2016/0279097 A1    Sep. 29, 2016

(30) Foreign Application Priority Data

Oct. 15, 2013  (EP) .................................... 13306415

(51) Int. Cl.
*A61K 38/26*    (2006.01)
*A61K 31/37*    (2006.01)
*A61K 31/255*   (2006.01)

(52) U.S. Cl.
CPC ............ *A61K 31/37* (2013.01); *A61K 31/255* (2013.01); *A61K 38/26* (2013.01); *A23V 2002/00* (2013.01)

(58) Field of Classification Search
CPC ..................................................... A61K 38/26
See application file for complete search history.

(56) References Cited

FOREIGN PATENT DOCUMENTS

| WO | WO 2007/127263 | 11/2007 | | |
|----|----|----|----|----|
| WO | WO 2012/088519 | 6/2012 | | |
| WO | WO 2012088519 A2 * | 6/2012 | ............ | A61K 36/185 |
| WO | WO-2012088519 A2 * | 6/2012 | ............ | A61K 36/185 |
| WO | WO-2014004902 A2 * | 1/2014 | ............. | A61K 45/06 |

OTHER PUBLICATIONS

Mayo Clinic. "Diabetes." © Jul. 31, 2014. Available from: < http://www.mayoclinic.org/diseases-conditions/diabetes/basics/prevention/con-20033091?p=1 >.*
Diabetes.co.uk. "Incretin Mimetics (GLP-1 analogues)." © Apr. 29, 2012. Available from: < https://web.archive.org/web/20120429072647/http://www.diabetes.co.uk/diabetes-medication/incretin-mimetics.html >.*
Diabetes.co.uk. "Diabetes Mellitus." © Mar. 19, 2011. Available from: < https://web.archive.org/web/20110319214731/http://www.diabetes.co.uk/diabetes-mellitus.html >.*
NetDoctor. "Glibenclamide." © Nov. 19, 2008. Available from: < https://www.netdoctor.co.uk/medicines/diabetes/a6512/glibenclamide/ >.*
Diabetes.co.uk. "Diabetes and Byetta (Exenatide)." © May 19, 2011. Available from: < https://web.archive.org/web/20110519134401/http://www.diabetes.co.uk/diabetes-medication/diabetes-and-byetta.html >.*
Harvard University. "Simple Steps to Preventing Diabetes." © 2017. Available from: < https://www.hsph.harvard.edu/nutritionsource/diabetes-prevention/preventing-diabetes-full-story/#T2D_can_be_prevented >.*
Diabetes.co.uk. "Diabetes Mellitus." © Mar. 19, 2011. Available from: < https://web.archive.org/web/20110319214731/http://www.diabetes.co.uk/diabetes-mellitus.html >. (Year: 2011).*
Diabetes.co.uk. "Incretin Mimetics (GLP-1 analogues)." © Apr. 29, 2012. Available from: < https://web.archive.org/web/20120429072647/http://www.diabetes.co.uk/diabetes-medication/incretin-mimetics.html >. (Year: 2012).*

(Continued)

*Primary Examiner* — Andrew D Kosar
*Assistant Examiner* — John S Kenyon
(74) *Attorney, Agent, or Firm* — Buchanan Ingersoll & Rooney PC

(57) ABSTRACT

The present invention relates to a composition comprising urolithin A, urolithin B, urolithin C, urolithin D, or a combination thereof, for the stimulation of insulin secretion, and to the use of a compound chosen among urolithin A, urolithin B, urolithin C, urolithin D, or a combination thereof, intended for the stimulation of insulin secretion. The present invention also relates to a composition comprising an effective amount of urolithin B, urolithin C, urolithin D, or a combination thereof, for the treatment or the prevention of diabetes mellitus, and in particular for the treatment or the prevention of type 2 diabetes, and to the use of a compound chosen among urolithin B, urolithin C, urolithin D, and a combination thereof, intended for the treatment or the prevention of diabetes mellitus, and in particular of type 2 diabetes.

3 Claims, 11 Drawing Sheets

(56) References Cited

OTHER PUBLICATIONS

Figure 1:
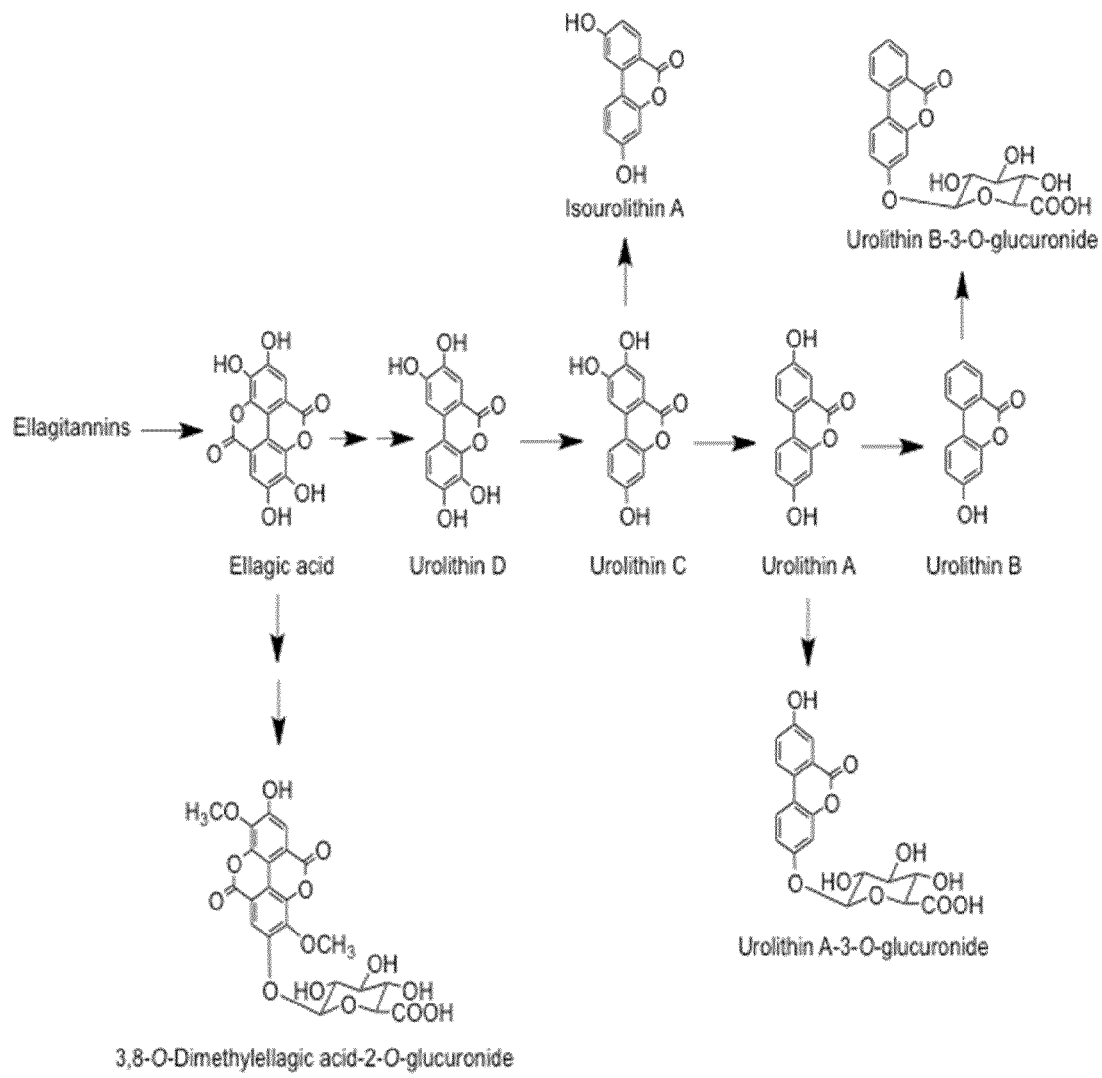
Figure 2A:
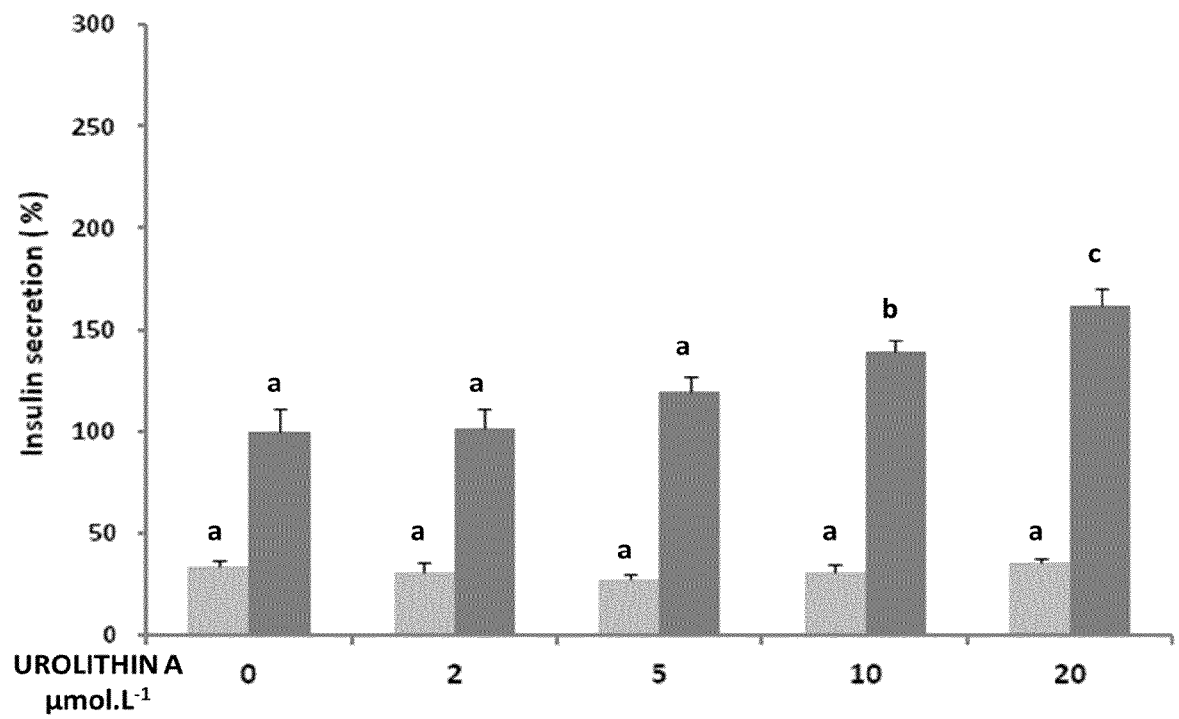
Figure 2B:
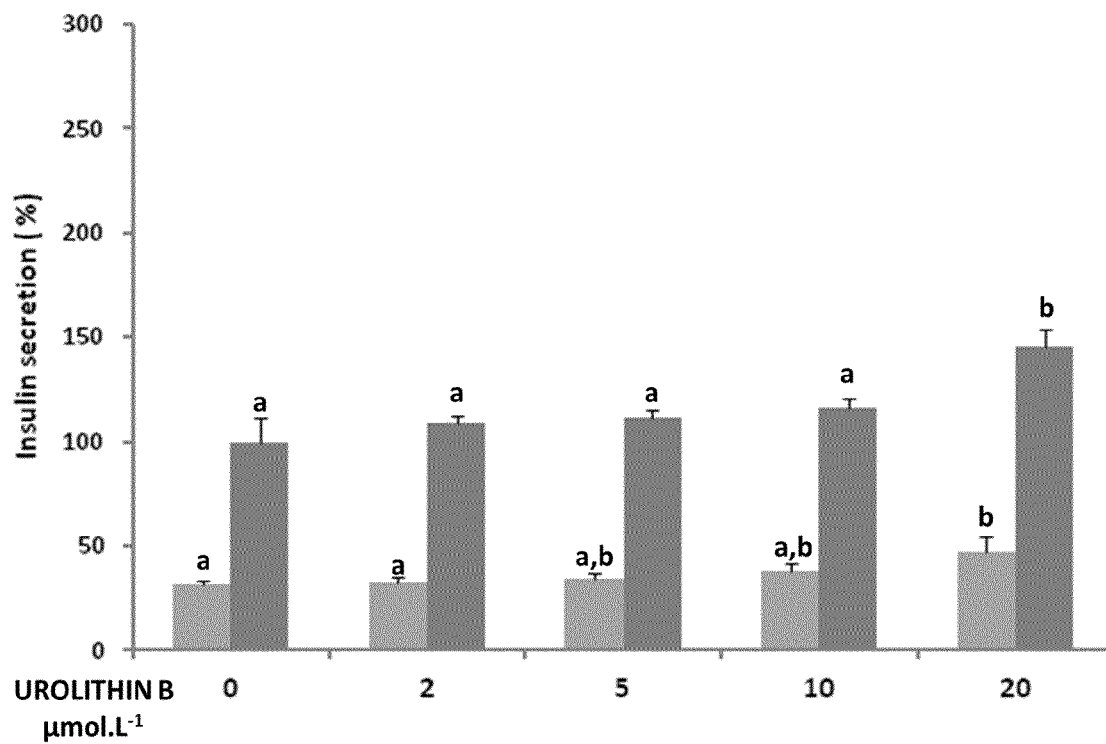
Figure 2C:
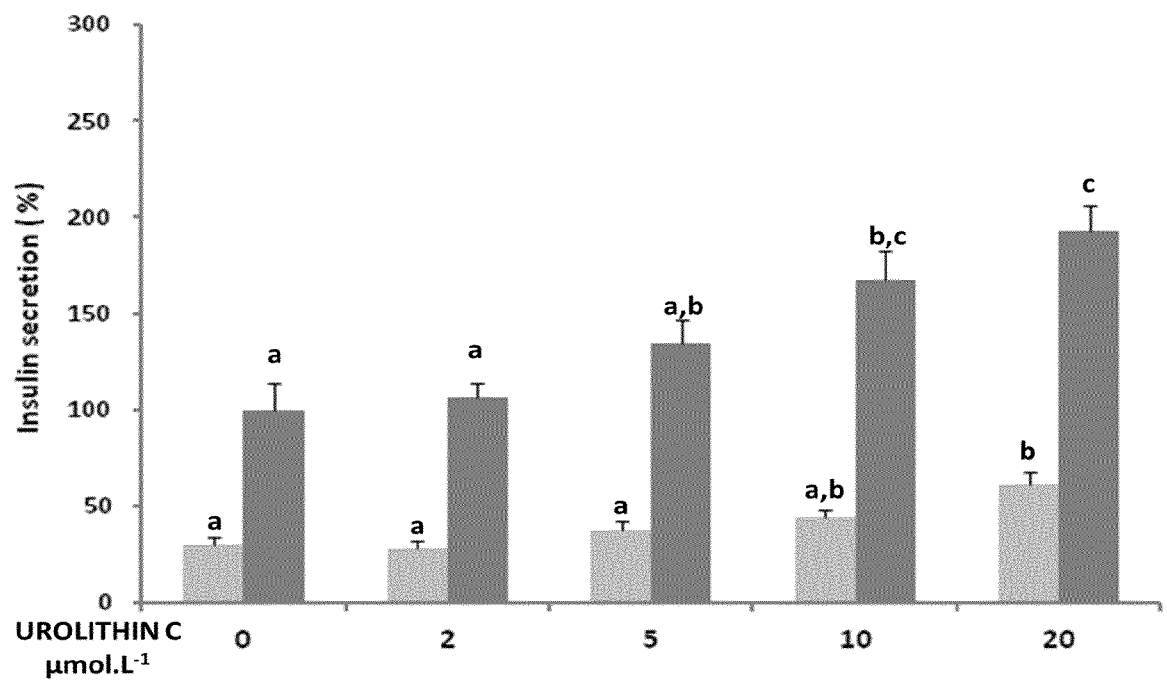
Figure 2D:
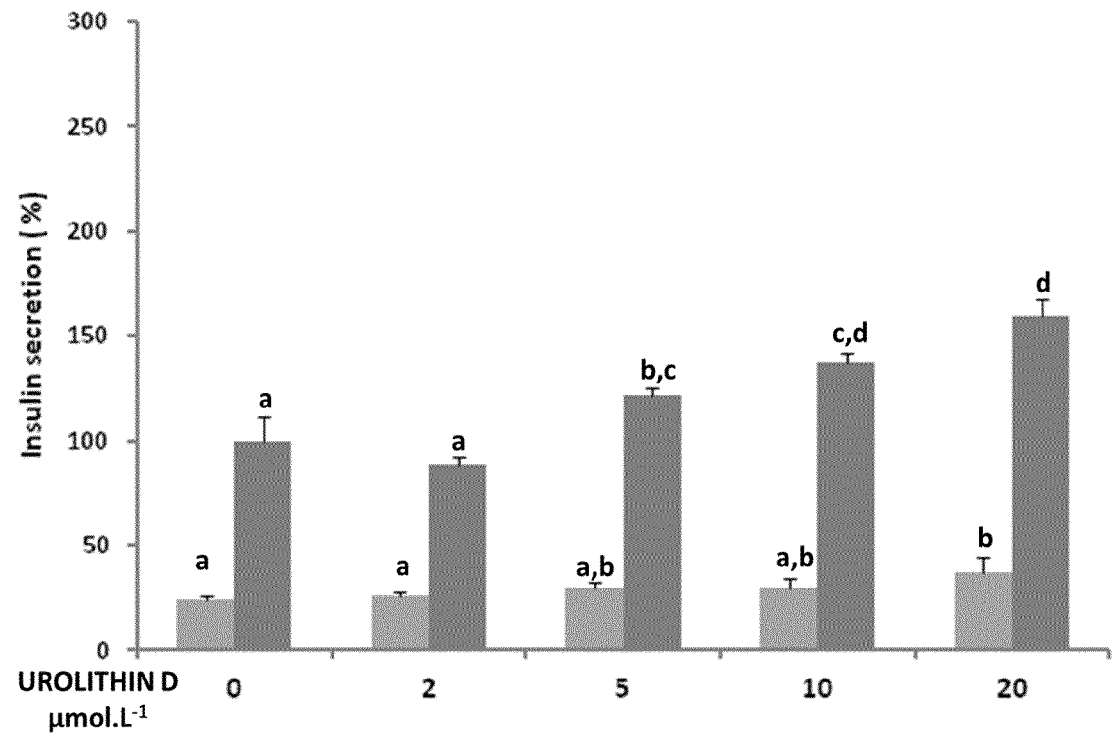
Figure 3A:
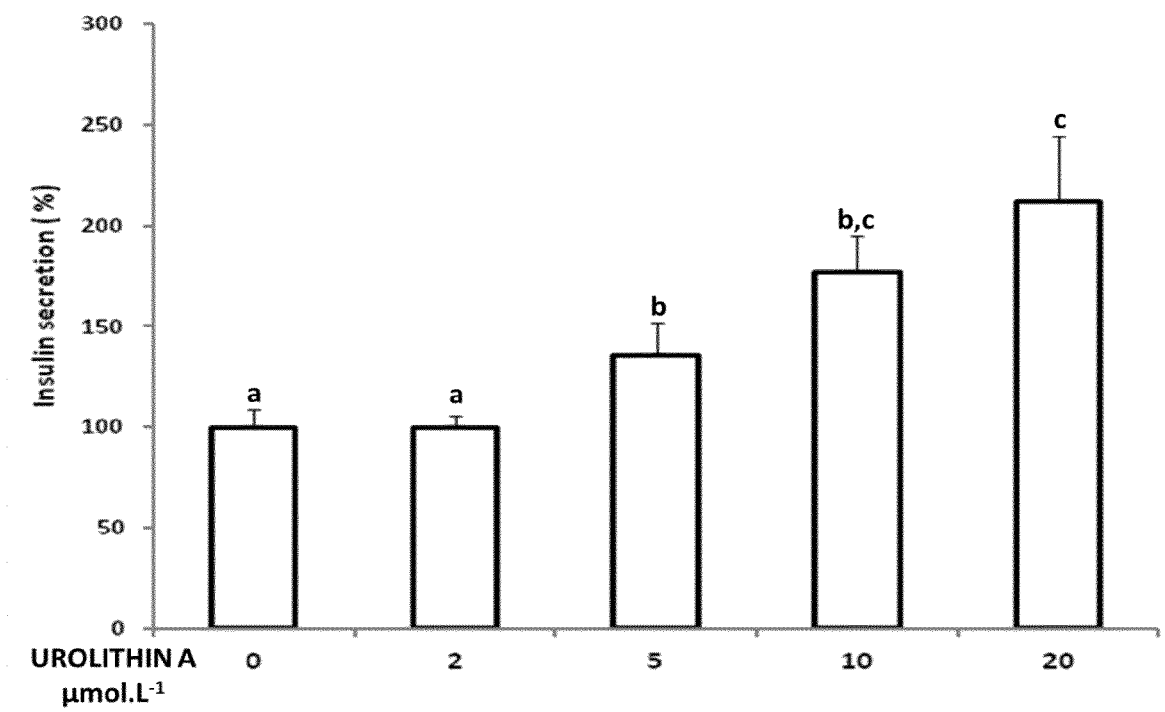
Figure 3B:
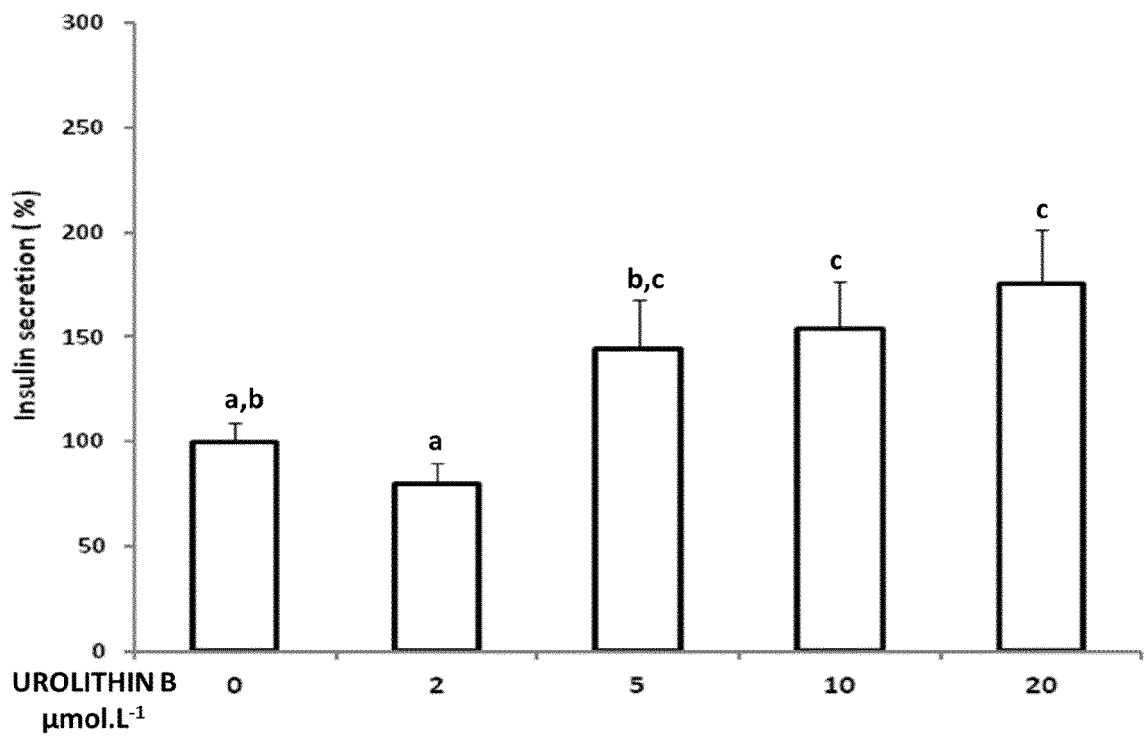
Figure 3C:
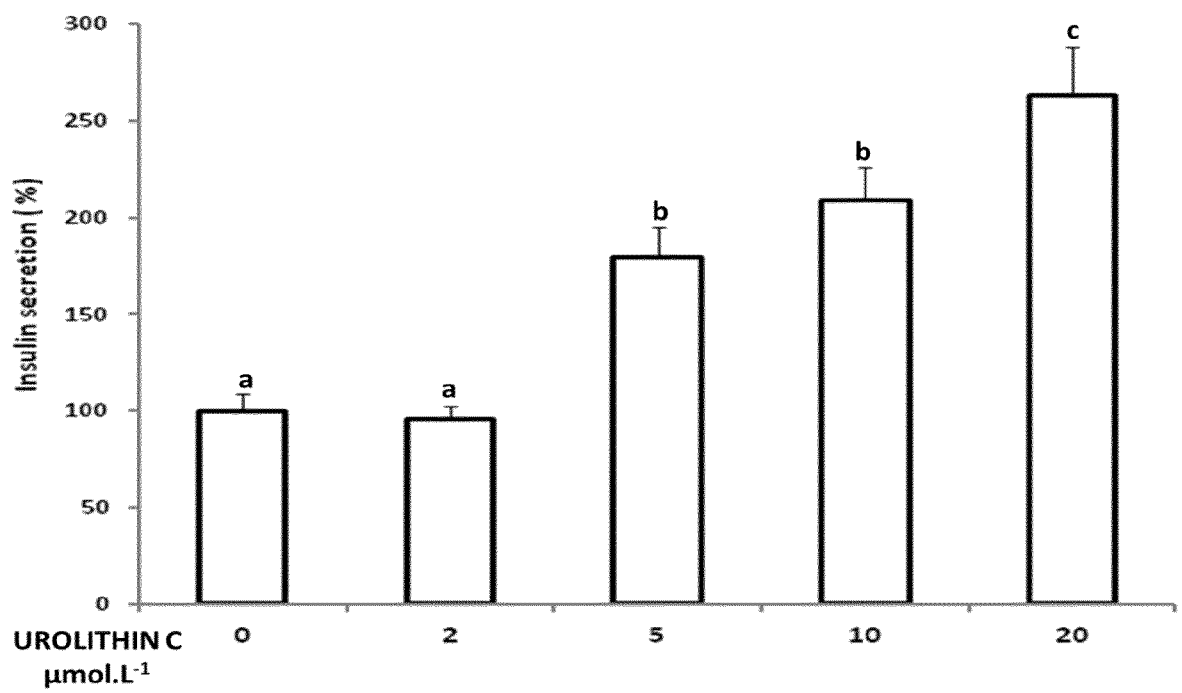
Figure 3D:
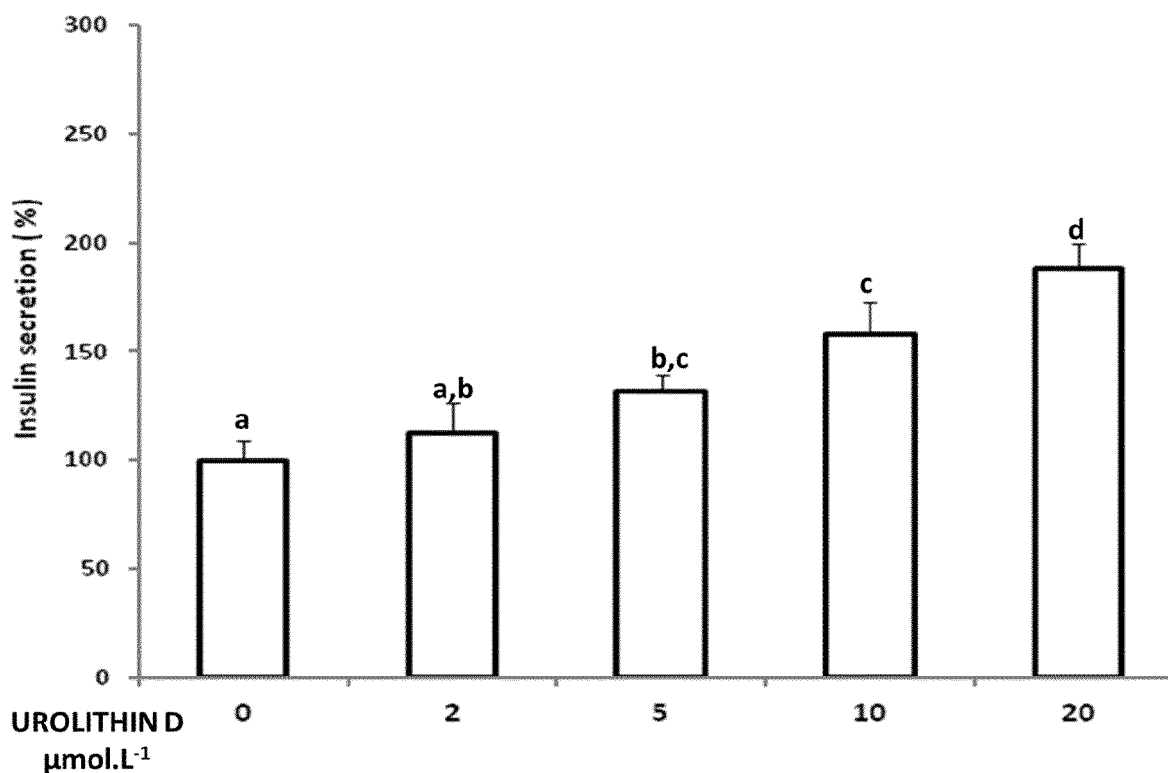

NetDoctor. "Glibenclamide." © Nov. 19, 2008. Available from: < http://www.netdoctor.co.uk/medicines/diabetes/a6512/glibenclamide/ >. (Year: 2008).*
Diabetes.co.uk. "Diabetes and Byetta (Exenatide)." © May 19, 2011. Available from: <https://web.archive.org/web/20110519134401/http://www.diabetes.co.uk/diabetes-medication/diabetes-and-byetta.html >. (Year: 2011).*
Tulane University School of Medicine. "DPP4 Inhibitors." (Aug. 30, 2013). Accessed Dec. 25, 2018. Available from: <http://tmedweb.tulane.edu/pharmwiki/doku.php/dpp-4_inhibitors >. (Year: 2013).*
Reddy, U. "Oral hypoglycemic agents." (Jun. 10, 2006). Accessed Dec. 25, 2018. Available from: < https://www.gwumc.edu/edu/obgyn/genetics/casestudies/Oral_hypoglycemic_agents.doc.htm >. (Year: 2006).*
Bardy et al., *Quercetin induces insulin secretion by direct activation of L-type calcium channels in pancreatic beta cells*, 169 British Journal of Pharmacology 1102-1113 (2013).
Bialonska et al., *Urolithins, Intestinal Microbial Metabolites of Pomegranate Ellagitannins, Exhibit Potent Antioxidant Activity in a Cell-Based Assay*, 57 J. Agric. Food Chem 10181-10186 (2009).
Bonora, *Protection of pancreatic beta-cells: Is it feasible?*, 18 Nutrition, Metabolism & Cardiovascular Diseases, 74-83 (2008).
Cadène et al., *Vanadyl sulphate differently influences insulin response to glucose in isolated pancreas of normal rats after in vivo or in vitro exposure*, 318 European Journal of Pharmacology 145-151 (1996).
Cerda et al., *The potent in vitro antioxidant ellagitannins from pomegranate juice are metabolised into bioavailable but poor antioxidant hydroxy-6H-dibenzopyran-6-one derivatives by the colonic microflora of healthy humans*, 43 Eur. J. Nutr. 205-220 (2004).
Cerdá et al., *Metabolism of Antioxidant and Chemopreventive Ellagitannins from Strawberries, Raspberries, Walnuts, and Oak-Aged Wine in Humans: Identification of Biomarkers and Individual Variability*, 53 J. Agric. Food Chem. 227-235 (2005).
Da Silva Pinto et al., *Evaluation of Antiproliferative, Anti-Type 2 Diabetes, and Antihypertension Potentials of Ellagitannins from Strawberries (FragariaXananassa Duch.) Using in Vitro Models*, 13(5) J. Med Food 1027-1035 (2010).
Del Rio et al., *Dietary (Poly)phenolics in Human Health: Structures, Bioavailability, and Evidence of Protective Effects Against Chronic Diseases*, 18(14) Antioxidants & Redox Signaling 1818-1892 (2013).
Del Rio et al., *Polyphenols and health: What compounds are involved?*, 20 Nutrition, Metabolism & Cardiovascular Diseases 1-6 (2010).
Garber, *Obesity and type 2 diabetes: which patients are at risk?*, 14 Diabetes, Obesity and Metabolism 399-408 (2012).
González-Sarrías et al., *The Gut Microbiota Ellagic Acid-Derived Metabolite Urolitin A and Its Sulfate Conjugate Are Substrates for the Drug Efflux Transporter Breast Cancer Resistance Protein (ABCG2/BCRP)*, 61 J. Agric. Food Chem. 4352-4359 (2013).
Kaneto et al., *Involvement of Oxidative Stress and the JNK Pathway in Glucose Toxicity*, 1(4) The Review of Diabetic Studies 165-174 (2004).
Li et al., *The sensitivity of pancreatic β-cells to mitochondrial injuries triggered by lipotoxicity and oxidative stress*, 36(5) Biochemical Society Transactions 930-934 (2008).
Lucas et al., *A concise synthesis of glucuronide metabolites of urolithin-B, resveratrol, and hydroxytyrosol*, 344 Carbohydrate Research 1340-1346 (2009).
Palsamy et al., *Resveratrol, a natural phytoalexin, normalizes hyperglycemia in streptozotocin-nicotinamide induced experimental diabetic rats*, 62 Biomedicine & Pharmacotherapy 598-605 (2008).
Poitout et al., *Glucolipotoxicity: Fuel Express and β-Cell Dysfunction*, 29(3) Endoc Rev. 351-366 (May 2008).
Tulipani et al., *Urolithins Are the Main Urinary Microbial-Derived Phenolic Metabolites Discriminating a Moderate Consumption of Nuts in Free-Living Subjects with Diagnosed Metabolic Syndrome*, 60 J. Agric. Food Chem. 8930-8940 (2012).
Verzelloni et al., *Antiglycative and neuroprotective activity of colon-derived polyphenol catabolites*, 55 Mol. Nutr. Food. Res. S35-S43 (2011).
Youl et al., *Quercetin potentiates insulin secretion and protects INS-1 pancreatic β-cells against oxidative damage via the ERK1/2 pathway*, 161 British Journal of Pharmacology 799-814 (2010).
International Search Report dated Jan. 9, 2015, in International Patent Application No. PCT/EP2014/072152.

* cited by examiner

COMPOSITIONS COMPRISING UROLITHINS AND USES THEREOF FOR THE STIMULATION OF INSULIN SECRETION

CROSS-REFERENCE TO RELATED APPLICATIONS

This application is a U.S. National Stage Application pursuant to 35 U.S.C. § 371 of International Patent Application PCT/EP2014/072152, filed on Oct. 15, 2014, and published as WO 2015/055736 on Apr. 23, 2015, which claims priority to European Patent Application 13306415.4, filed on Oct. 15, 2013, all of which are incorporated herein by reference in their entireties for all purposes.

The present invention first relates to a composition comprising urolithin A, urolithin B, urolithin C, urolithin D or a combination thereof intended for its use for the stimulation of insulin secretion, and to a composition comprising urolithin B, urolithin C, urolithin D or a combination thereof intended for its use for the treatment or the prevention of diabetes mellitus.

Diabetes mellitus comprises type 1 diabetes and type 2 diabetes. Type 2 diabetes is defined by an increase of fasting and/or post prandial glycemia (or blood glucose level), and is due to a combination of two factors: a resistance to the effect of insulin and a progressive impairment of insulin secretion. Hyperglycemia occurs when insulin secretion by pancreatic insulin-secreting β-cells from the endocrine pancreas becomes progressively impaired and unable to compensate for insulin resistance. Protection of pancreatic β-cells is therefore essential to change the natural history of diabetes after the onset of the disease but may also be crucial in preventing or delaying the onset on the disease in at-risk, or prediabetic, subjects.

"At-risk to become diabetic" or "prediabetic" patients are defined as having a fasting glycemia between 1 and 1.25 $g \cdot L^{-1}$ (5.5 to 6 9 $mmol \cdot L^{-1}$) (including the limits) and a post-prandial glycemia between 1.40 and 1.99 $g \cdot L^{-1}$ (7.7 to 10.9 $mmol \cdot L^{-1}$), wherein diabetic patients are defined by fasting glycemia and post-prandial glycemia levels superior to pre-diabetic patients levels, respectively.

On the basis of these criteria, it is estimated that there are currently, in the United States of America, 70 millions of pre-diabetic patients and 25.8 millions of diabetic patients. Noticeably, two-thirds of pre-diabetic patients having both fasting and post-prandial criteria will become diabetic patients.

Identifying and treating prediabetic patients, in order to prevent the occurrence of diabetes, has become a major public health issue (Garber, 2012). Oxidative stress, caused by an increase in intracellular reactive oxygen species (ROS) plays a central role in pancreatic β-cells death during the progressive deterioration of glucose tolerance and development of type 2 diabetes (Li et al., 2008; Poitout and Robertson, 2008). Attempts have been made with various drugs used in established type 2 diabetes to prevent the occurrence of diabetes in at-risk patients. Although some positive results were obtained, a compound both efficient and devoid of long term side-effects is still required. Interestingly, one of the mechanisms involved in those preventive trials was the protection of β-cells from insults induced by oxidative stress (Bonora, 2008).

Protective actions of polyphenol metabolites and catabolites against human chronic diseases, such as cancer and inflammation, have been described (Del Rio et al., 2012). Del Rio et al. (2012) discloses the structure and bioavailability of urolithins A, B, C and D, and their mechanism in models related to cancer and inflammation, but it does not disclose nor suggest the use of urolithin A, B, C or D for the treatment or prevention of diabetes type 2 nor for the stimulation of insulin secretion.

Quercetin, a polyphenolic flavonoid, is known to display anti-diabetic properties in vivo, and it has been demonstrated that quercetin increases insulin secretion in a concentration-dependent manner (Youl et al., 2010; Bardy et al., 2013). Other data suggest that polyphenols display some anti-diabetic properties: resveratrol was shown to normalize hyperglycemia in diabetic rats (Palsamy and Subramanian, 2008). Also, it has been shown that treatment using the antioxidant N-acetyl-L-cysteine (NAC) can improve the control of glycemia (Kaneto et al., 1999). However, quercetin, but not resveratrol nor NAC, potentiates both glucose and glibenclamide-induced insulin secretion (Youl et al., 2010). Quercetin, but not resveratrol nor NAC, also prevents the impairment of viability and insulin secretion induced by oxidative stress on β-cells (Youl et al., 2010).

Pinto et al. (2010) discloses the potential use of ellagitannins and of ellagic acid for the treatment of hyperglycemia and hypertension linked to type 2 diabetes.

There is still a need for food compositions or pharmaceutical compositions able to stimulate insulin secretion and/or to be used for the prevention or the treatment of diabetes mellitus. Ideally, stimulation of insulin secretion should occur under hyperglycemic, but not under normoglycemic conditions, in order to avoid the occurrence of hypoglycemia, which is a frequent side-effect happening with current insulin secreting drugs such as sulfonylureas.

This is the object of the present invention.

WO 2012/088519 discloses C57BL6/J mice fed with a high-fat diet (HFD), resulting in obesity and type 2 diabetes, wherein the administration of punicalagin, ellagic acid and urolithin A mixed with the food improved glucose tolerance in said HFD mice. WO 2012/088519 discloses urolithin A for the treatment or prevention of diabetes mellitus. However, this document does not disclose the use of urolithin B, C or D for the treatment or prevention of diabetes mellitus nor of type 2 diabetes and does not disclose the use of urolithin A, B, C or D for the stimulation of insulin secretion.

The inventors have demonstrated, in a model of insulin-secreting β-cells, that urolithin A, urolithin B, urolithin C and urolithin D are unexpectedly able to significantly stimulate insulin secretion, contrarily to their precursor, ellagic acid. In particular, the inventors demonstrated that urolithins are able to potentiate glucose-induced insulin secretion and drug-induced insulin secretion, in the presence of a sulfonylurea and of a GLP-1 analog. Urolithins B, C and D amplified insulin secretion in all experimental conditions at the maximal concentration tested, whereas urolithin A does not stimulate insulin secretion under low-glucose condition in this model. The degree of amplification by urolithins appears similar in the glucose- and glibenclamide-stimulating conditions, suggesting that those compounds act as amplifiers of insulin secretion stimulants, $EC_{50}$'s being around 5 to 10 $\mu mol \cdot L^{-1}$. herefore, urolithins can be considered as amplifiers of glucose-or drug-induced insulin secretion. Also, in the presence of a GLP-1 analog, the addition of urolithin C or of urolithin D does lead to a significant raise of insulin secretion. Therefore, the present invention provides new compositions able to potentiate the effect of two different and widely used treatments for diabetes and insulin secretion stimulants, such as sulfonylurea and GLP-1 derivatives.

In the same model, the inventors have also demonstrated that urolithins are able to prevent the occurrence of oxidative stress-induced insulin secretion and viability impairments, which are two factors important in the progressive degradation of β-cells insulin secreting capacities leading to occurrence of diabetes or its progressive worsening. Urolithins C and D appear more active on viability and urolithins B and C are more active on insulin secretion.

In a physiologically relevant model that mimics the in vivo situation, the rat isolated perfused pancreas, the inventors also showed that urolithins induced insulin secretion. Again, urolithin C was the most active compound. Interestingly, secretory effects occurred at a 8.3 mmol·L$^{-1}$ (or 1.5 g·L$^{-1}$) stimulating concentration of glucose, but not at a 5 mmol·L$^{-1}$ (or 0.9 g·L$^{-1}$) non-stimulating concentration of glucose (equivalent to fasting normoglycemia). This is an important feature suggesting that urolithins will not induce hypoglycemia, a frequent side-effect occurring with the use of insulin secretion-stimulating drugs such as sulfonylureas, which induce insulin secretion (and subsequent hypoglycemia) even under normoglycemic conditions.

Thus, the present invention provides compositions comprising urolithin A, urolithin B, urolithin C and urolithin D, alone or in combination, that present a nutritional and/or a therapeutic interest for the stimulation of insulin secretion and/or for the prevention or the treatment of diabetes mellitus, and in particular of type 2 diabetes.

The present invention will become more fully understood from the detailed description given herein and from the accompanying drawings, which are given by way of illustration only and do not limit the intended scope of the invention.

The present invention first relates to a composition intended for its use for the stimulation of insulin secretion comprising at least one urolithin chosen in the group consisting of: urolithin A, urolithin B, urolithin C, urolithin D and a combination thereof.

In a particular embodiment, a composition intended for its use for the stimulation of insulin secretion, according to the invention, comprises an effective amount of at least one urolithin chosen in the group consisting of: urolithin A, urolithin B, urolithin C, urolithin D and a combination thereof.

The term "effective amount" as used herein, pertains to the amount of an active compound which is effective for producing some desired effect.

By "urolithin" or "urolithins" it is intended a series of metabolites produced by the transformation within the intestinal lumen, and by yet unidentified micro-organisms, of ellagic acid (EA). In the present application "urolithin" or "urolithins" may be used as a general term to designate one or several of the following compounds: urolithin A, urolithin B, urolithin C urolithin D and their isomers, including iso-urolithin A. Urolithin A, urolithin B, urolithin C and urolithin D may also be designated as "Uro A", "Uro B", "Uro C" and "Uro D" respectively. The structure of urolithin A (dihydroxydibenzopyranone), urolithin B (monohydroxydibenzopyranone), urolithin C (trihydroxydibenzopyranone), urolithin D (tetrahydroxydibenzopyranone) and isourolithin A is represented in FIG. 1.

Urolithins are metabolites of ellagic acid (EA), of punicalagin, punicalin, tellimagrandin and other ellagitannins (Cerda et al., 2004; Cerda et al., 2005) Urolithins share a 6H-dibenzo[b,d]pyran-6-one structural nucleus with at least a hydroxyl group. Cleavage and decarboxylation of the lactone ring and different specific dehydroxylations of the EA nucleus account for the whole range of urolithins. As a result, urolithins exhibit a different phenolic hydroxylation pattern. Transformation of EA starts in the small intestine, specifically in the jejunum, and the first metabolite produced, urolithin D, retains four phenolic hydroxyls. The metabolism continues along the gastrointestinal tract with the sequential removal of hydroxyl groups, leading to the production of urolithin C, urolithin A, and finally urolithin B in the distal parts of the colon (see FIG. 1). It has been shown that urolithins are absent in biological fluids of ileostomy subjects but present in urine excreted by healthy volunteers, indicating the colon as the site of formation of these EA-derived catabolites in humans. In addition, in vitro faecal incubations have served to clarify the microbial origin of these metabolites as well as to demonstrate the production of only urolithin aglycones by microbiota-mediated breakdown of EA.

In a particular embodiment, a composition intended for the stimulation of insulin secretion, according to the invention, comprises an effective amount of at least one urolithin chosen in the group consisting of: urolithin B, urolithin C, urolithin D and a combination thereof.

In a particular embodiment, in a composition according to the present invention, urolithin is provided as an isolated urolithin, which may be obtained in particular by chemical synthesis, then purified or at least partially purified, or from purification from a natural source.

Urolithins may be synthesized de novo, as described in the present application and in Bialonska et al. (2009).

By "stimulation of insulin secretion" it is intended the induction of a higher level of secreted insulin in the presence of urolithin, when compared to the level of secreted insulin in the absence of urolithin. Preferably, a composition according to the invention is intended for the in vivo stimulation of insulin secretion after administration to a mammal, and preferably a human being. A composition according to the invention is also intended for the in vitro stimulation of insulin secretion of isolated β-cells. A higher level of secreted insulin may consist for example in a more rapidly induced, stronger or more sustained insulin secretion.

In a particular embodiment, the present invention relates to a composition comprising at least one urolithin chosen in the group consisting of: urolithin A, urolithin B, urolithin C, urolithin D and a combination thereof, a intended for its use for the amplification of the stimulation of insulin secretion.

By "amplification of the stimulation of insulin secretion" it is intended the induction of a higher level of secreted insulin in the presence of urolithin and of a compound able to stimulate insulin secretion when compared to the level of secreted insulin in the presence of said compound able to stimulate insulin secretion but in the absence of urolithin. A compound able to stimulate insulin secretion designates for example, glucose, when present at an effective concentration in blood to stimulate insulin secretion, a sulfonylurea, a GLP-1 analog or a DPP4 inhibitor.

In another embodiment, the present invention relates to a composition intended for its use for the stimulation of insulin secretion comprising a combination of two urolithins chosen in the group consisting of: urolithin A, urolithin B, urolithin C and urolithin D. In another embodiment, the present invention relates to a composition intended for its use for the stimulation of insulin secretion comprising a combination of three urolithins chosen in the group consisting of: urolithin A, urolithin B, urolithin C and urolithin D. In another embodiment, the present invention relates to a composition intended for its use for the stimulation of insulin secretion comprising a combination of urolithin A, urolithin B, urolithin C and urolithin D.

In another particular embodiment, the present invention relates to a composition intended for its use for the treatment or the prevention of diabetes mellitus comprising at least one urolithin chosen in the group consisting of: urolithin B, urolithin C, urolithin D and a combination thereof.

In a particular embodiment, a composition intended for the treatment or the prevention of diabetes mellitus, according to the invention, comprises an effective amount of at least one urolithin chosen in the group consisting of: urolithin B, urolithin C, urolithin D and a combination thereof.

"Diabetes mellitus" or "diabetes", is a group of chronic metabolic diseases wherein patients are characterized by a high level of blood sugar, which may arise either because of insufficient production of insulin by pancreas or by an absence, or unsufficient response of insulin target cells to the insulin produced. Type 1 diabetes results from a primary failure of endocrine pancreas to produce insulin (immunologically-induced disappearance of (β-cells), and requires the person to receive insulin. Type 2 diabetes results both from insulin resistance, in which insulin target cells fail to respond to insulin properly, and from the progressive failure of the β-cells to produce an appropriate amount of insulin to control glycemia. Gestational diabetes is observed when pregnant women develop a high blood glucose level in the absence of a previous diagnosis of diabetes.

In a particular embodiment, the present invention relates to a composition intended for its use for the treatment or the prevention of type 2 diabetes mellitus comprising at least one urolithin chosen in the group consisting of: urolithin B, urolithin C, urolithin D and a combination thereof.

In a particular embodiment, the present invention relates to a composition intended for its use for the treatment or the prevention of diabetes mellitus, and in particular of type 2 diabetes, comprising a combination of an effective amount of two urolithins chosen in the group consisting of: urolithin A, urolithin B, urolithin C and urolithin D. In another embodiment, the present invention relates to a composition intended for its use for the treatment or the prevention of diabetes mellitus comprising a combination of an effective amount of three urolithins chosen in the group consisting of: urolithin A, urolithin B, urolithin C and urolithin D. In another embodiment, the present invention relates to a composition intended for its use for the treatment or the prevention of diabetes mellitus comprising a combination of an effective amount of urolithin A, urolithin B, urolithin C and urolithin D.

In a particular embodiment, the present invention relates to a composition intended for its use for the amplification of a drug-induced stimulation of insulin secretion, comprising of urolithin A, urolithin B, urolithin C, urolithin D or a combination thereof. In a more particular embodiment, the present invention relates to a composition intended for its use for the amplification of a drug-induced stimulation of insulin secretion comprising urolithin A, urolithin B, urolithin C, urolithin D or a combination thereof, wherein said drug is chosen in the group consisting of sulfonylureas and GLP-1 analogs.

In a more particular embodiment, the invention relates to a composition intended for its use for the stimulation of insulin secretion or for the treatment or the prevention of diabetes mellitus comprising an effective amount of at least one urolithin chosen in the group consisting of: urolithin A, urolithin B, urolithin C, urolithin D and a combination thereof, wherein at least one of said urolithin is chemically modified.

In a more particular embodiment, a composition according to the invention intended for its use for the stimulation of insulin secretion or for the treatment or the prevention of diabetes mellitus comprises an effective amount of at least one urolithin chosen in the group consisting of: urolithin A, urolithin B, urolithin C, urolithin D and a combination thereof, wherein said at least one chemically modified urolithin is chosen in the group consisting of: glucuronidated urolithin, methylated urolithin, sulfated urolithin.

The preparation of glucuronidated urolithin, of methylated urolithin and of sulfated urolithin disclosed in Lucas et al. (2009), and in Tulipani et al. (2012).

In a particular embodiment, the present invention relates to a composition comprising at least one urolithin chosen in the group consisting of urolithin A, urolithin B, urolithin C, urolithin D or a combination thereof, intended for its use for the stimulation of insulin secretion, and to a composition comprising at least one urolithin chosen in the group consisting of urolithin B, urolithin C, urolithin D or a combination thereof, intended for its use for the treatment or the prevention of diabetes mellitus, wherein the treated patient is chosen among: a prediabetic patient, a patient whose fasting glycemia is comprised between 1 g·L$^{-1}$ (5.55 mmol·L$^{-1}$) and 1.25 g/l (6.89 mmol/l) and a patient whose post prandial glycemia is comprised between 1.40 g·L$^{-1}$ (7.7 mmol·L$^{-1}$) and 1.99 g/l (10.95 mmol·L$^{-1}$).

A prediabetic patient is a patient diagnosed with pre-diabetes or a patient at risk for diabetes.

The term "fasting glycemia" designates glucose concentration in blood after a fasting period, preferably after a 8 hours, a 10 hours or a 12 hours fast.

The term "post prandial glycemia" designates glucose concentration in blood after a meal, preferably 2 hours after a meal.

The determination of glycemia in a method according to the invention can be performed by any glucose test known by a man skilled in the art of blood tests and of diabetes and prediabetes. These methods include, without restriction the use of a known device described as a glucose meter.

In another particular embodiment, the present invention relates to a composition comprising at least one urolithin chosen in the group consisting of urolithin A, urolithin B, urolithin C, urolithin D or a combination thereof, intended for its use for the stimulation of insulin secretion, and to a composition comprising at least one urolithin chosen in the group consisting of urolithin B, urolithin C, urolithin D or a combination thereof, intended for its use for the treatment or the prevention of diabetes mellitus, wherein the treated patient is chosen among: a diabetic patient, a patient whose fasting glycemia is equal or superior to 1.26 g·L$^{-1}$ (7 mmol·L$^{-1}$) and a patient whose post prandial glycemia equal superior to 2 g·L$^{-1}$ (11 mmol·L$^{-1}$).

The present invention also relates to the use of a composition comprising an effective amount of at least one urolithin chosen in the group consisting of: urolithin A, urolithin B, urolithin C, urolithin D and a combination thereof, for preparing a food product, a nutritional supplement or a pharmaceutical composition.

The present invention also relates to a composition for the stimulation of insulin secretion comprising an effective amount of at least one urolithin chosen in the group consisting of: urolithin A, urolithin B, urolithin C, urolithin D and a combination thereof, wherein said composition is a food product, a nutritional supplement or a pharmaceutical composition.

The present invention relates to a food product or a nutritional supplement for the stimulation of insulin secretion comprising an effective amount of at least one urolithin chosen in the group consisting of: urolithin A, urolithin B, urolithin C, urolithin D and a combination thereof.

The present invention also relates to a food product or a nutritional supplement for the prevention or treatment of diabetes comprising an effective amount of at least one urolithin chosen in the group consisting of: urolithin A, urolithin B, urolithin C, urolithin D and a combination thereof.

By "food product", "dietary supplement" or "nutritional supplement" it is intended to designate a product intended to complement a normal diet to be administered orally, comprising a composition according to the invention, comprising an effective amount of at least one urolithin chosen in the group consisting of: urolithin A, urolithin B, urolithin C, urolithin D and a combination thereof, and a nutritionally acceptable vehicle.

The term "nutritionally acceptable" as used herein pertains to compounds, ingredients, materials, compositions, dosage forms, etc., which are suitable for use in contact with the tissues of the subject in question (e.g. human) without excessive toxicity, irritation, allergic response, or side-effect commensurate with a reasonable benefit/risk ratio. The compositions herein may a composition according to the invention, alone or in combination with a carrier, delivery system, excipient or diluent that is acceptable for nutritional usage. The following galenic forms can be envisaged: swallowable tablets, chewable tablets, effervescent tablets, capsules, pills, powders, granules, oral solutions or suspensions, and sublingual and buccal dosage forms.

In a particular embodiment, the present invention relates to a pharmaceutical composition comprising an effective amount of at least one urolithin chosen in the group consisting of: urolithin A, urolithin B, urolithin C, urolithin D and a combination thereof, and a pharmaceutically acceptable vehicle.

By "pharmaceutical composition" it is intended to designate a product to be administered orally or parenterally to a subject, and characterized by a preventive or therapeutic effect observed on subjects.

A composition according to the invention may be administered to a subject by any convenient route of administration, said administration being possibly: systemic, peripheral, topic, oral or parenteral.

Administration can be effected in one dose, continuously or intermittently throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the individual planning the treatment.

According to a particular embodiment, a composition according to the invention is administered in a dose equal or equivalent to 0.01 to 150 milligram (mg) urolithin per kilogram (kg) body weight. More preferably, a composition according to the invention is administered in a dose equal or equivalent to 0.1 to 120 mg urolithin per kg body weight. More preferably, a composition according to the invention is administered in a dose equal or equivalent to 1 to 120 mg urolithin per kg body weight. More preferably, a composition according to the invention is administered in a dose equal or equivalent to 4 to 90 mg urolithin per kg body weight. Even more preferably, a composition according to the invention is administered in a dose equal or equivalent to 8 to 30 mg urolithin per kg body weight.

While it is possible for the active compound to be used (e.g., administered) alone, it is often preferable to present it as a formulation. The formulations may be prepared by any methods well known in the art of pharmacy. Such methods include the step of bringing into association the active compound with a carrier which constitutes one or more accessory ingredients. Suitable formulations, carriers, diluents, excipients, etc. are known by one of skilled in the art.

The present invention also relates to a composition comprising at least one urolithin chosen among urolithin A, urolithin B, urolithin C, urolithin D and a combination thereof, and a compound able to stimulate insulin secretion, intended for its use for the stimulation of insulin secretion.

In a particular embodiment, the present invention relates to a composition comprising at least one urolithin chosen among urolithin A, urolithin B, urolithin C, urolithin D and a combination thereof, and a compound able to stimulate insulin secretion chosen among sulfonylureas, GLP-1 analogs and DPP4 inhibitors, intended for its use for the stimulation of insulin secretion.

In a more particular embodiment, the present invention relates to a composition comprising:
at least one urolithin chosen among urolithin A, urolithin B, urolithin C, urolithin D and a combination thereof, and
glibenclamide,
intended for its use for the stimulation of insulin secretion.

In an even more particular embodiment, the present invention relates to a composition comprising urolithin C and glibenclamide, intended for its use for the stimulation of insulin secretion.

In another more particular embodiment, the present invention relates to a composition comprising:
at least one urolithin chosen among urolithin A, urolithin B, urolithin C, urolithin D and a combination thereof, and
exendin,
intended for its use for the stimulation of insulin secretion.

In an even more particular embodiment, the present invention relates to a composition comprising urolithin C and exendin, intended for its use for the stimulation of insulin secretion.

The present invention also relates to a composition comprising at least one urolithin chosen among urolithin B, urolithin C, urolithin D and a combination thereof, and a compound able to stimulate insulin secretion, intended for its use for the prevention or the treatment of diabetes mellitus.

In a particular embodiment, the present invention relates to a composition comprising at least one urolithin chosen among urolithin B, urolithin C, urolithin D and a combination thereof, and a compound able to stimulate insulin secretion chosen among sulfonylureas, GLP-1 analogs and DPP4 inhibitors, intended for its use for the prevention or the treatment of diabetes mellitus.

In a more particular embodiment, the present invention relates to a composition comprising:
at least one urolithin chosen among urolithin B, urolithin C, urolithin D and a combination thereof, and
glibenclamide,
intended for its use for the prevention or the treatment of diabetes mellitus.

In an even more particular embodiment, the present invention relates to a composition comprising urolithin C and glibenclamide, intended for its use for the prevention or the treatment of diabetes mellitus.

In another more particular embodiment, the present invention relates to a composition comprising:
  at least one urolithin chosen among urolithin A, urolithin B, urolithin C, urolithin D and a combination thereof, and
  exendin,
intended for its use for the prevention or the treatment of diabetes mellitus.

In an even more particular embodiment, the present invention relates to a composition comprising urolithin C and exendin, intended for its use for the prevention or the treatment of diabetes mellitus.

In an even more particular embodiment, the present invention relates to a composition comprising urolithin C and exendin, intended for its use for the prevention or the treatment of type 2 diabetes. The present invention also relates to the use of a composition comprising an effective amount of at least one urolithin chosen in the group consisting of: urolithin A, urolithin B, urolithin C, urolithin D and a combination thereof, for the stimulation of insulin secretion.

More particularly, the present invention relates to the use of a composition comprising an effective amount of at least one urolithin chosen in the group consisting of: urolithin A, urolithin B, urolithin C, urolithin D and a combination thereof, for the in vivo stimulation of insulin secretion.

The present invention relates to the use for the stimulation of insulin secretion, of a composition comprising a combination of an effective amount of two urolithins chosen in the group consisting of urolithin A, urolithin B, urolithin C and urolithin D. The present invention relates to the use for the stimulation of insulin secretion, of a composition comprising a combination of an effective amount of three urolithins chosen in the group consisting of urolithin A, urolithin B, urolithin C and urolithin D. The present invention relates to the use for the stimulation of insulin secretion, of a composition comprising a combination of an effective amount of urolithin A, urolithin B, urolithin C and urolithin D for the stimulation of insulin secretion.

In another embodiment, the present invention relates to the use of a composition comprising an effective amount of at least one urolithin chosen in the group consisting of: urolithin B, urolithin C, urolithin D and a combination thereof, for the treatment or prevention of diabetes mellitus.

In a particular embodiment, the present invention relates to a method for the treatment of diabetes comprising the administration of urolithin B, urolithin C or urolithin D, alone or in combination, to a subject or a patient in need thereof.

In a particular embodiment, the present invention relates to a method for the treatment of diabetes comprising the administration of urolithin B, urolithin C or urolithin D, alone or in combination, to a subject in need thereof, wherein said subject or patient is also administered with a treatment intended to stimulate insulin secretion.

In a particular embodiment, the present invention relates to a method for the treatment of diabetes comprising the administration of urolithin B, urolithin C or urolithin D, alone or in combination, to a subject in need thereof, wherein said subject is administered with a treatment intended to stimulate insulin secretion, said treatment being chosen in the group of sulfonylureas or of GLP-1 analogs.

In a particular embodiment, the present invention relates to a method for the treatment of diabetes comprising the administration of urolithin C or urolithin D, alone or in combination, to a subject in need thereof, wherein said subject is administered with a treatment intended to stimulate insulin secretion, said treatment being chosen in the group of GLP-1 analogs.

In a particular embodiment, the present invention relates to a composition for the stimulation of insulin secretion, said composition comprising, for a simultaneous, sequential or successive use, an effective amount of at least one urolithin chosen among urolithin A, urolithin B, urolithin C, urolithin D and a combination thereof, and a compound able to stimulate insulin secretion.

In a particular embodiment, the present invention relates to a composition for the stimulation of insulin secretion, said composition comprising, for the simultaneous, sequential or successive use, an effective amount of at least one urolithin chosen among urolithin A, urolithin B, urolithin C, urolithin D and a combination thereof, and a compound able to stimulate insulin secretion, said compound being chosen in the group consisting of sulfonylureas, meglitinides and other ligands of $K^+$ ATP channels.

Sulfonylureas are drugs used for stimulating insulin secretion which contain a central S-phenylsulfonylurea structure with a p-substituent on the phenyl ring and various groups terminating the urea N' end group.

In a particular embodiment, the present invention relates to a composition for the stimulation of insulin secretion, said composition comprising, for a simultaneous, sequential or successive use, an effective amount of at least one urolithin chosen among urolithin A, urolithin B, urolithin C, urolithin D and a combination thereof, and a sulfonylurea chosen in the group consisting of: Metahexamide, Glibenclamide (Glyburide), Carbutamide, Acetohexamide, Chlorpropamide, Tolbutamide, Tolazamide, Glipizide, Gliclazide, Glibornuride, Gliquidone, Glisoxepide, Glyclopyramide and Glimepiride.

In a more particular embodiment, the present invention relates to a composition for the stimulation of insulin secretion, said composition comprising, for a simultaneous, sequential or successive use, an effective amount of at least one urolithin chosen among urolithin A, urolithin B, urolithin C, urolithin D and a combination thereof, and glibenclamide (glyburide).

In a more particular embodiment, the present invention relates to a composition for the stimulation of insulin secretion, said composition comprising, for a simultaneous, sequential or successive use, an effective amount of urolithin C, urolithin D and glibenclamide (glyburide).

In an even more particular embodiment, the present invention relates to a composition for the stimulation of insulin secretion, said composition comprising, for a simultaneous, sequential or successive use, an effective amount of urolithin C, and glibenclamide (glyburide).

In an even more particular embodiment, the present invention relates to a composition for the stimulation of insulin secretion, said composition comprising, for a simultaneous, sequential or successive use, an effective amount of urolithin D, and glibenclamide (glyburide).

In an even more particular embodiment, the present invention relates to a composition for the stimulation of insulin secretion, said composition comprising, for a simultaneous, sequential or successive use, an effective amount of urolithin A, and glibenclamide (glyburide).

In another particular embodiment, the present invention relates to a composition for the stimulation of insulin secretion, said composition comprising, for a simultaneous, sequential or successive use, an effective amount of at least one urolithin chosen among urolithin A, urolithin B, urolithin C, urolithin D and a combination thereof, and a compound chosen in the group of meglitinide, wherein said meglitinide is chosen in the group consisting: Nateglinide, Repaglinide and Mitiglinide.

In a particular embodiment, the present invention relates to a composition for the stimulation of insulin secretion, said composition comprising, for a simultaneous, sequential or successive use, an effective amount of at least one urolithin chosen among urolithin A, urolithin B, urolithin C, urolithin D and a combination thereof, and a compound able to stimulate insulin secretion chosen in the group consisting of GLP-1 agonists.

By "GLP-1 agonists", "Glucagon-like peptide-1 agonists" or "GLP-1 derivatives" it is intended a class of drugs also known as "incretin mimetics".

In a more particular embodiment, the present invention relates to a composition for the stimulation of insulin secretion, said composition comprising, for a simultaneous, sequential or successive use, an effective amount of at least one urolithin chosen among urolithin A, urolithin B, urolithin C, urolithin D and a combination thereof, and a GLP-1 analog chosen in the group consisting of: exenatide (exendin, Byetta) and liraglutide (Victoza), or any other GLP-1 analog.

In an even more particular embodiment, the present invention relates to a composition for the stimulation of insulin secretion, said composition comprising, for a simultaneous, sequential or successive use, an effective amount of urolithin C and exenatide.

In another particular embodiment, the present invention relates to a composition for the stimulation of insulin secretion, said composition comprising, for a simultaneous, sequential or successive use, an effective amount of urolithin D and exenatide.

In a particular embodiment, the present invention relates to a composition for the stimulation of insulin secretion, said composition comprising, for a simultaneous, sequential or successive use, an effective amount of at least one urolithin chosen among urolithin A, urolithin B, urolithin C, urolithin D and a combination thereof, and a compound able to stimulate insulin secretion chosen in the group consisting of DPP4-inhibitors.

By "DPP4 inhibitors" it is intended enzyme inhibitors that inhibit the enzyme dipeptidyl peptidase-4 (DPP-4) that selectively binds substrates that contain proline at the P1-position. More particularly, a DPP-4 inhibitor has 5-membered heterocyclic rings that mimic proline, such as: pyrrolidine, cyanopyrrolidine, thiazolidine and cyanothiazolidine groups. Inhibition of the DPP-4 enzyme prolongs and enhances the activity of incretins that play an important role in insulin secretion and blood glucose control regulation.

In a more particular embodiment, the present invention relates to a composition for the stimulation of insulin secretion, said composition comprising, for a simultaneous, sequential or successive use, at least one urolithin chosen among the group consisting of urolithin A, urolithin B, urolithin C, urolithin D and a DPP4 inhibitor chosen in the group consisting of: Alogliptin, Gemigliptin, Linagliptin, Saxagliptin, Sitagliptin and Vildagliptin.

In a more particular embodiment, the present invention relates to a composition for the prevention or for the treatment of diabetes mellitus, said composition comprising, for a simultaneous, sequential or successive use, an effective amount of at least one urolithin chosen among the group consisting of urolithin B, urolithin C, urolithin D and a combination thereof, and a compound usable for the prevention or the treatment of diabetes mellitus.

In a more particular embodiment, the present invention relates to a composition for the prevention or for the treatment of diabetes mellitus, said composition comprising, for a simultaneous, sequential or successive use, an effective amount of at least one urolithin chosen among the group consisting of urolithin B, urolithin C, urolithin D and a combination thereof, and a compound usable for the prevention or the treatment of diabetes mellitus, wherein said diabetes mellitus is type 2 diabetes.

In a more particular embodiment, the present invention relates to a composition for the prevention or for the treatment of diabetes mellitus, said composition comprising, for a simultaneous, sequential or successive use, an effective amount of at least one urolithin chosen among the group consisting of urolithin B, urolithin C, urolithin D and a combination thereof, and a compound usable for the prevention or the treatment of diabetes mellitus, chosen in the group consisting of: a compound able to stimulate insulin secretion, an insulin-sensitizer compound, an insulin analog, an alpha-glucosidase inhibitor, an amylin analog and a SGLT2 inhibitor.

In a particular embodiment, the present invention relates to a composition for the prevention or for the treatment of diabetes mellitus, said composition comprising, for a simultaneous, sequential or successive use, an effective amount of at least one urolithin chosen among the group consisting of urolithin B, urolithin C, urolithin D and a combination thereof, and a compound able to stimulate insulin secretion chosen in the group consisting of sulfonylureas, meglitinides and other ligands of $K^+$ ATP channels.

In a particular embodiment, the present invention relates to a composition for the prevention or for the treatment of diabetes mellitus, said composition comprising, for the simultaneous, sequential or successive use, an effective amount of at least one urolithin chosen among the group consisting of urolithin B, urolithin C, urolithin D and a combination thereof, and an insulin-sensitizer compound chosen in the group consisting of biguanides, PPAR and dual PPAR agonists.

In another particular embodiment, the present invention relates to a composition for the prevention of the treatment of diabetes mellitus, said composition comprising, for a simultaneous, sequential or successive use, at least one urolithin chosen among the group consisting of urolithin B, urolithin C, urolithin D and a combination thereof, and a biguanide, wherein said biguanide is Metformin (N,N-Dimethylimidodicarbonimidic diamide, Glucophage®, Stagid® or their generic form) or an analog thereof.

The present invention also relates to a kit for the in vitro stimulation of insulin secretion comprising the following elements:

i) at least one compound chosen in the group consisting of : urolithin A, urolithin B, urolithin C, urolithin D and a combination thereof, and ii) reagents for the determination of the presence of secreted insulin.

The following examples are provided herein for purposes of illustration only and are not intended to be limiting unless otherwise specified.

LEGENDS OF THE FIGURES

FIG. 1: Representation of potential pathways for the conversion of ellagitannins to urolithins The acorn ellagitannins release ellagic acid, which is metabolized sequentially by intestinal microbiota, producing urolithin D, urolithin C, urolithin A and urolithin B.

FIGS. 2A to 2D: Histogram representation of the concentration-response study of urolithins on insulin secretion determined in INS-1 insulin-secreting β-cells on insulin secretion under low-glucose (1.4 mmol·L$^{-1}$) or glucose-stimulated (8.3 mmol·L$^{-1}$) secretion conditions.

FIGS. 2A-D illustrate the effects of urolithin A (FIG. 2A), urolithin B (FIG. 2B), urolithin C (FIG. 2C) or urolithin D (FIG. 2D) on insulin secretion determined under low-glucose (1.4 mmol·L$^{-1}$, left bars) or glucose (8.3 mmol·L$^{-1}$)-stimulated secretion (right bars) conditions. Data are expressed as percentage of insulin secretion in the presence of 8.3 mmol·L$^{-1}$ glucose alone ("control 100%"). In each case, insulin secretion was determined in the presence of urolithins at concentrations varying from 0 to 20 μmol·L$^{-1}$. Results are presented as means±SEM of 4-6 separate experiments. A multiple comparison analysis of data was performed for each experimental condition. For each figure, different letters at the top of the bars correspond to statistically significant differences ($p<0.05$) between data obtained under the same experimental conditions.

FIGS. 3A to 3D: Histogram representation of the concentration-response effect of urolithins on insulin secretion determined in INS-1 insulin-secreting β-cells, in the presence of glibenclamide.

FIGS. 3A-D illustrate the effects of urolithin A (FIG. 3A), urolithin B (FIG. 3B), urolithin C (FIG. 3C) or urolithin D (FIG. 3D) on insulin secretion determined in the presence of 1.4 mmol·L$^{-1}$ glucose and 0.01 μmol·L$^{-1}$ glibenclamide. In each case, insulin secretion was determined in the presence of urolithins at concentrations varying from 0 ("control 100%") to 20 μmol·L$^{-1}$. Results are presented as means±SEM of 4-6 separate experiments. A multiple comparison analysis of data was performed for each experimental condition. For each figure, different letters at the top of the bars correspond to statistically significant differences ($\rho<0.05$) between data obtained under the same experimental conditions.

FIGS. 4A to 4D: Histogram representation of the concentration-response effect of urolithins on insulin secretion determined in INS-1 insulin-secreting β-cells in the presence of exendin.

FIGS. 4A-D illustrate the effects of urolithin A (FIG. 4A), urolithin B (FIG. 4B), urolithin C (FIG. 4C) or urolithin D (FIG. 4D) on insulin secretion determined in the presence of 8.3 mmol·L$^{-1}$ glucose and 0.001 μmol·L$^{-1}$ exendin. In each case, insulin secretion was determined in the presence of urolithins at concentrations varying from 0 ("control 100%") to 20 μmol·L$^{-1}$. Results are presented as means±SEM of 4-6 separate experiments. A multiple comparison analysis of data was performed for each experimental condition. For each figure, different letters at the top of the bars correspond to statistically significant differences ($p<0.05$) between data obtained under the same experimental conditions.

FIGS. 5A to 5D: Histogram representation of the concentration-response effect of urolithins on insulin secretion determined in INS-1 insulin-secreting β-cells in the presence of oxidative stress.

FIGS. 5A-D illustrate the effects of urolithin A (FIG. 5A), urolithin B (FIG. 5B), urolithin C (FIG. 5C) or urolithin D (FIG. 5D) on insulin secretion determined in the presence of 8.3 mmol·L$^{-1}$ glucose and 50 μmol·L$^{-1}$ H$_2$O$_2$. In each case, insulin secretion was determined in the presence of urolithins at concentrations varying from 0 to 20 μmol·L$^{-1}$. Data are expressed as percentage of insulin secretion determined in the presence of 8.3 mmol·L$^{-1}$ glucose ("control 100%"). Results are presented as means±SEM of 3 determinations. A multiple comparison analysis of data was performed for each experimental condition. For each figure, different letters at the top of the bars correspond to statistically significant differences ($p<0.05$) between data obtained under the same experimental conditions.

Figure 6:
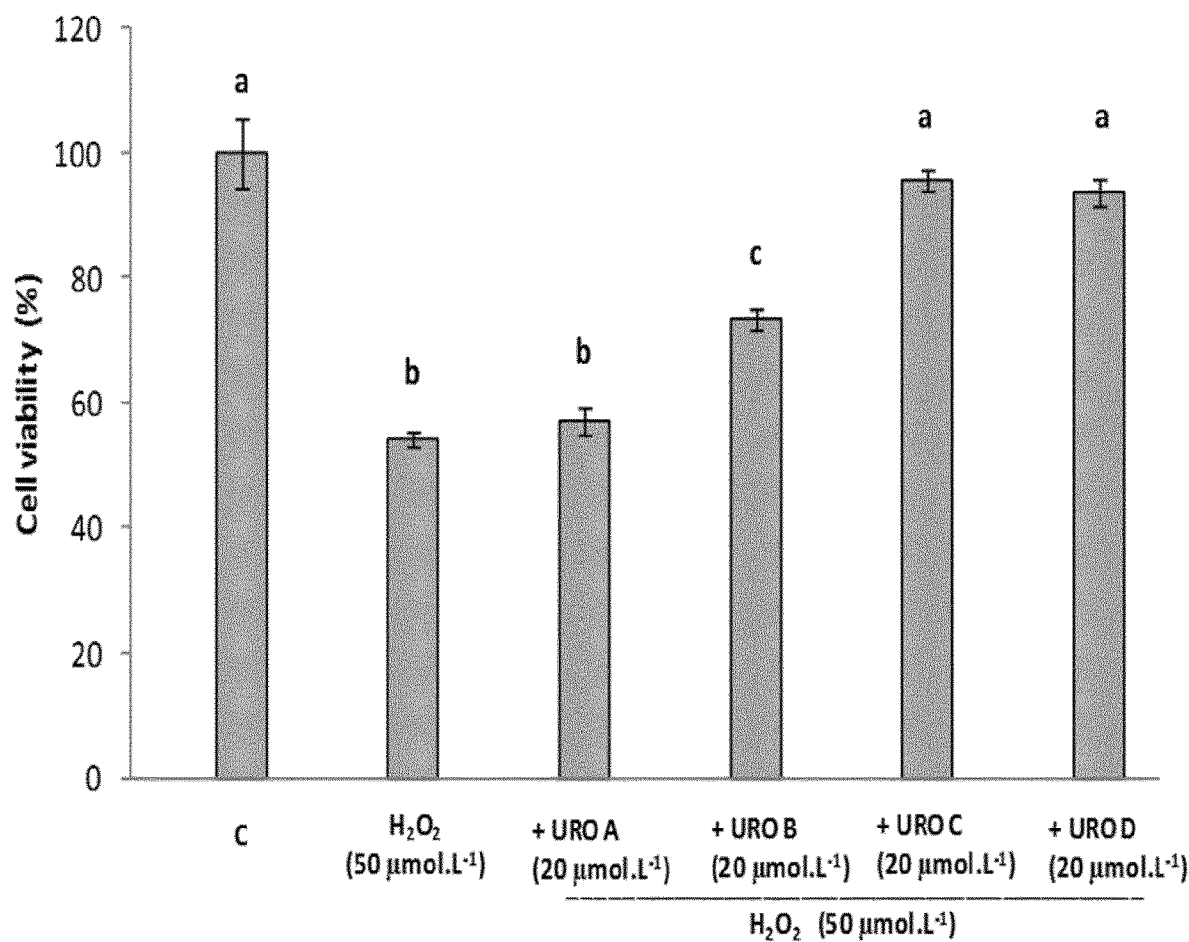

FIG. 6: Histogram representation of the effect of urolithins on cell viability determined in INS-1 insulin-secreting β-cells in the presence of oxidative stress.

FIG. 6 illustrates the effects of 20 μmol·L$^{-1}$ of urolithin A, urolithin B, urolithin C or urolithin D on cell viability determined in the presence of 8.3 mmol·L$^{-1}$ glucose and 50 μmol·L$^{-1}$ H$_2$O$_2$. Data are expressed as percentage of cell viability determined in the presence of 8.3 mmol·L$^{-1}$ glucose ("control 100%"). Results are presented as means±SEM of 4 determinations. A multiple comparison analysis of data was performed for each experimental condition. Different letters at the top of the bars correspond to statistically significant differences ($p<0.05$) between data obtained under the same experimental conditions.

Figure 7A:
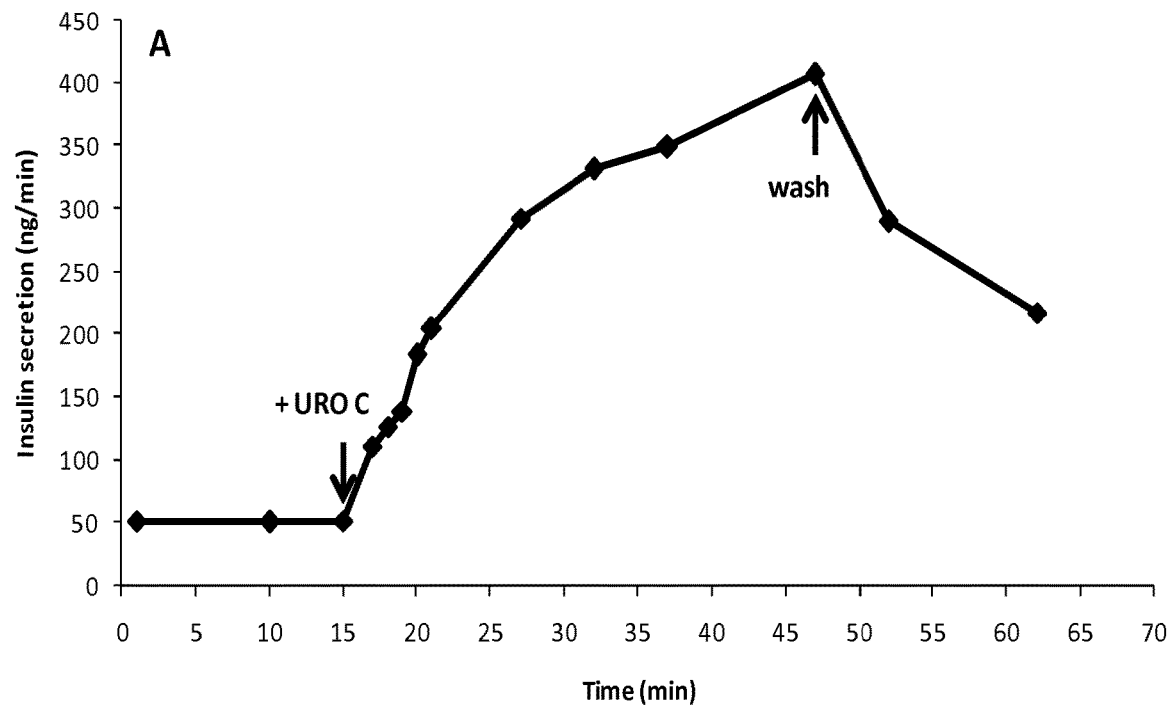
Figure 7B:
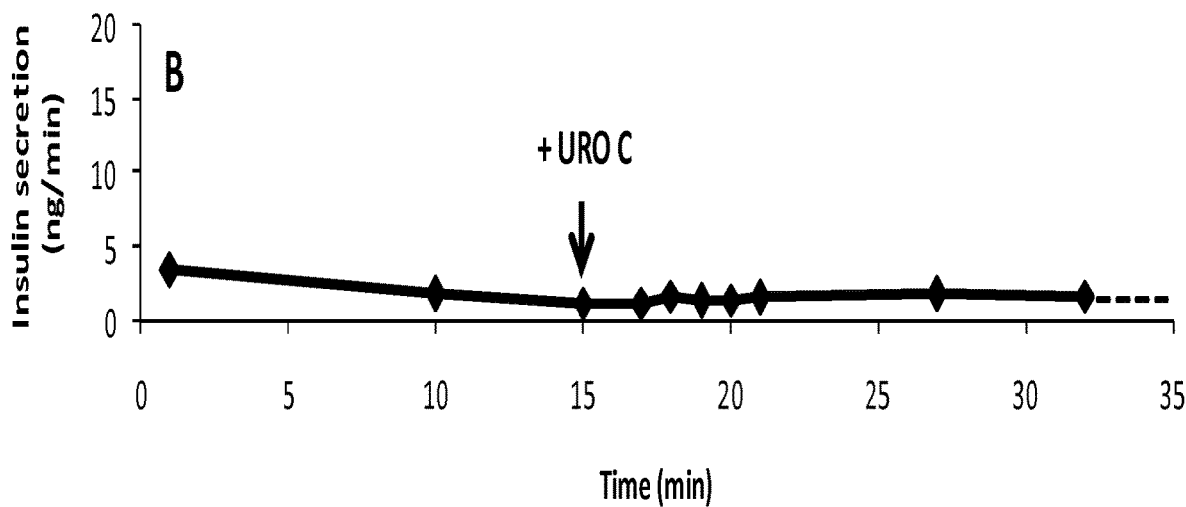

FIG. 7A and 7B: Effect of urolithin C on insulin secretion determined in the rat isolated perfused pancreas.

FIGS. 7A and 7B illustrate the effect of urolithin C (10 μmol·L$^{-1}$) under 8.3 or 5 mmol·L$^{-1}$ glucose conditions, respectively. Rat pancreas was surgically isolated and perfused (2.5 ml/min) with modified Krebs-Ringer bicarbonate buffer containing 8.3 mmol·L$^{-1}$ (FIG. 7A) or 5 mmol·L$^{-1}$ (FIG. 7B) glucose in the absence or presence of urolithin C (10 μmol·L$^{-1}$). Samples collected for 1 minute were taken at the indicated times and insulin concentration determined (HTRF insulin assay kit, Cisbio International, Bagnols-sur-Ceze, France). Amounts of insulin (ng) secreted per minute are indicated as a function of time (minutes).

EXAMPLES

Example 1

Insulin Secretion in the Presence of Catabolites and Metabolites of Polyphenols in the INS-1 Insulin Secreting β-Cells 30 polyphenol metabolites (see Table I), used at the concentrations of 2 and 20 μmol·L$^{-1}$, were blind-screened for their capacities to modulate glucose (8.3 mmol·L$^{-1}$)-stimulated insulin secretion. In table I, data are expressed as percent of glucose (8.3 mmol·L$^{-1}$)-stimulated secretion ("internal standard").

Obtention of molecules:

Urolithins A and B were synthesized by Cu$^{II}$-mediated coupling of 1,3-dihydroxybenzene and 2-bromo- 5-hydroxybenzoic acid (urolithin A) or 2-bromobenzoic acid (urolithin B) in concentrated aqueous NaOH according to already reported procedures (Bialonska D. et al., 20092-Bromo-5-hydroxybenzoic acid was obtained from commercially available 2-bromo-5-methoxybenzoic acid through demethylation by BBr3 (3 equiv.) in CH$_2$Cl$_2$/hexane (3:2, v/v) at low temperature (−20 to 0° C.). Urolithins were isolated by precipitation and their purity checked by HPLC analysis. Their NMR and MS characteristics were in agreement with the literature. Urolithin C and D were purchased from Dalton Pharma Services (Toronto, Canada) and the certificates of analysis are available. Other compounds were commercially available.

Reagents for the determination of insulin secretion

RPMI-1640 media, fetal calf serum (FCS), HEPES solution, sodium pyruvate solution and Dulbecco's phosphate buffered (PBS) were purchased from Lonza (Levallois Perret, France). All the other chemicals and compounds as dimethyl sulfoxide (DMSO), 2-mercaptoethanol, L-glutamine-penicillin- streptomycin solution, albumin from bovine serum (BSA), poly-L-lysine, HEPES, $NaHCO_3$, $KH_2PO_4$, NaCl, KCl, $CaCl_2$, $MgSO_4$, exendin and glibenclamide were obtained from Sigma-Aldrich (St. Louis, Mo., USA).

INS-1 cell culture

The insulin-secreting cell line INS-1 (a gift from Professor C. B. Wollheim) was cultured in RPMI- 1640, supplemented with 10% fetal calf serum (FCS), 100 $U·mL^{-1}$ penicillin, 100 $µg·mL^{-1}$ streptomycin, 2 $mmol·L^{-1}$ L-glutamine, 10 $mmol·L^{-1}$ HEPES, 1 $mmol·L^{-1}$ sodium pyruvate, and 50 $mmol·L^{-1}$ 2-mercaptoethanol, as previously described by Youl et al. (2010). Cells were seeded in 24-well plates ($4×10^5$ cells per well) and were used for experiments after 5 days of culture.

Determination of insulin secretion

Before the treatment, RPMI medium was removed and the cells were washed twice with HEPES-balanced Krebs-Ringer bicarbonate buffer (KRB) containing (in $mmol·L^{-1}$): 123 NaCl, 5.4 KCl, 1.3 $KH_2PO_4$, 2.7 $MgSO_4$, 2.9 $CaCl_2$, 5 $NaHCO_3$ and 20 HEPES, pH 7.5, with 2 $g·L^{-1}$ bovine serum albumin (KRB/BSA). Cells were incubated for 1 h (5% $CO_2$, 37° C.) in KRB medium containing 8.3 $mmol·L^{-1}$ glucose (glucose-stimulated secretion) in the presence or absence of the compounds tested. At the end of the 1 h incubation period, the medium was sampled and stored at −20° C. until the insulin assay. Insulin concentration in cell supernatants was determined using the homogeneous time resolved fluorescence technology (HTRF), according to the manufacturer's instructions (HTRF insulin assay kit, Cisbio International, Bagnols-sur-Ceze, France). Briefly, two anti-insulin antibodies were used; one labelled with $Eu^{3+}$-Cryptate and one labelled with XL665 recognizing distinct epitopes. When these two fluorophores bind to insulin molecules, the two antibodies come into close proximity, allowing fluorescence resonance energy transfer (FRET) to occur between the $Eu^{3+}$-Cryptate and the XL665. This FRET increases proportionally with the insulin concentrations. All the experiments were performed at least in quadruplicate.

Results

Result of blind-screening of polyphenols metabolites are indicated on Table I which shows the effect of various human phase II and colonic metabolites/catabolites of polyphenols on glucose (8.3 $mmol·L^{-1}$)-stimulated insulin secretion. A positive control, quercetin, was tested under the same conditions. Control response corresponds to insulin secretion determined in the presence of 8.3 $mmol·L^{-1}$ glucose alone.

TABLE I

| Metabolites/Catabolites | % control response | |
|---|---|---|
| | 2 µM | 20 µM |
| From flavonols | | |
| Phloroglucinol | 100.00 | 105.00 |
| Protocatechuic acid | 108.00 | 92.00 |
| 4-hydroxybenzoic acid | 96.00 | 98.00 |
| 3,4-dihydroxyphenylacetic acid | 105.00 | 84.00 |
| Quercetin-3-glucuronide | 89.00 | 103.00 |
| Kaempferol-3-glucuronide | 111.00 | 104.00 |
| From chlorogenic acids | | |
| Caffeic acid | 104.00 | 105.00 |
| Dihydrocaffeic acid | 110.00 | 83.00 |

TABLE I-continued

| Metabolites/Catabolites | % control response | |
|---|---|---|
| | 2 µM | 20 µM |
| Ferulic acid | 109.00 | 115.00 |
| Dihydroferulic acid | 106.00 | 103.00 |
| Feruloylglycine | 102.00 | 102.00 |
| Isoferuloylglycine | 80.00 | 82.00 |
| From flavan-3-ols | | |
| 4'-hydroxyphenylacetic acid | 102.00 | 74.00 |
| 3-O-Methylgallic acid | 93.00 | 105.00 |
| 4-O-Methylgallic acid | 104.00 | 86.00 |
| Pyrogallol | 93.00 | 98.00 |
| Homovanillic acid | 93.00 | 83.00 |
| From cyanidin-based anthocyanins | | |
| Tyrosol | 86.00 | 89.00 |
| 4'-hydroxyhippuric acid | 98.00 | 111.00 |
| 3-(4'-hydroxyphenyl)lactic acid | 97.00 | 79.00 |
| 3-(3'-hydroxyphenyl)propionic acid | 98.00 | 103.00 |
| 3-hydroxyphenylacetic acid | 98.00 | 104.00 |
| 4'-hydroxyphenylacetic acid | 107.00 | 81.00 |
| Pyrocatechol | 87.00 | 96.00 |
| 4'hydroxymandelic acid | 103.00 | 86.00 |
| From sanguiin H-6 ellagitanin | | |
| Urolithin A (URO A) | 109.82 | 162.50 |
| Urolithin B (URO B) | 108.77 | 145.61 |
| Urolithin C (URO C) | 107.14 | 194.64 |
| Urolithin D (URO D) | 88.79 | 158.62 |
| Ellagic acid | 93.36 | 100.92 |
| Quercetin (positive control) | 93.80 | 237.00 |

The blind screening of 30 polyphenolic metabolites indicates that the only metabolites/catabolites able to amplify glucose (8.3 $mmol·L^{-1}$)-stimulated insulin secretion are urolithins A, B, C and D. The urolithin precursor, ellagic acid, is not active.

Example 2

Effect of Urolithins A, B, C or D Determined in INS-1 Insulin Secreting β-Cells in the Presence of Low Glucose (1.4 $mmol·L^{-1}$) or Glucose (8.3 $mmol·L^{-1}$)-Stimulated Secretion Conditions (FIGS. 2A-D).

In the experiments described below, concentration-response studies of active compounds selected from example 1 were performed and reproduced four times under low-glucose (1.4 $mmol·L^{-1}$) or glucose (8.3 $mmol·L^{-1}$)-stimulated secretion conditions.

Material and methods were the same as described in example 1. For the determination of insulin secretion, cells were incubated for 1h (5% $CO_2$, 37° C.) in KRB medium containing either 1.4 $mmol·L^{-1}$ glucose (low-glucose) or 8.3 $mmol·L^{-1}$ glucose (glucose-stimulated secretion) in the presence or absence of the compounds tested. At the end of the 1 h incubation period, mediums were sampled and stored at −20° C. until the insulin assay. Insulin concentration in cell supernatants was determined as described in Example 1.

Data are expressed as percent of glucose (8.3 $mmol·L^{-1}$)-stimulated secretion ("control 100%") in FIGS. 2A-D.

Results:

In low-glucose condition, urolithin A did not significantly stimulate insulin secretion while urolithins B, C and D induced some stimulation at the maximal concentration tested (20 $µmol·L^{-1}$). In glucose-stimulated secretion condition, urolithin C appeared as the compound producing the greatest stimulation (about 200%) at the maximal concentration tested (20 µmol·L$^{-1}$). Regarding active concentrations, urolithins A, C and D displayed a clear concentration-dependent effect, the concentration inducing 50% of the maximal stimulation (EC$_{50}$) being around 5 to 10 µmol·L$^{-1}$. Urolithin B was active for 20 µmol·L$^{-1}$ only.

Example 3

Effect of Urolithins A, B, C or D Determined in INS-1 Insulin Secreting β-Cells in the Presence of Glibenclamide (FIGS. 3A-D)

Glibenclamide is an insulin secretion stimulant sulfonylurea used in the treatment of diabetes. Like other sulfonylureas, glibenclamide is able to stimulate insulin secretion even at low glucose concentrations. In the experiments described below, glibenclamide concentration (0.01 µmol·L$^{-1}$) was chosen as able to induce a 4/6-fold increase of secretion as compared to low-glucose condition.

Material and methods were the same as described in example 1. For the determination of insulin secretion, cells were incubated for 1 h (5% $CO_2$, 37° C.) in KRB medium containing 1.4 mmol·L$^{-1}$ glucose (low-glucose condition) and 0.01 µmol·L$^{-1}$ glibenclamide (glibenclamide-stimulated secretion), in the presence or absence of urolithins. At the end of the 1 h incubation period, the medium was sampled and stored at −20° C. until the insulin assay. Insulin concentration in cell supernatants was determined as described in Example 1.

Data are expressed as percent of glibenclamide-stimulated insulin secretion ("control 100%") in FIGS. 3A-D.
Results:

In the presence of glibenclamide, urolithins A, B, C and D concentration-dependently stimulated insulin secretion, again with some differences regarding amplitude of responses and active concentrations. Regarding maximal response, urolithin C appeared as the most active compound (about 200% stimulation as compared to glibenclamide alone), followed by urolithins A/D (150-160%) and B (130%). Regarding active concentrations, maximal effect was obtained for urolithin A at 5 µmol·L$^{-1}$. For the same concentration, urolithin C stimulated glibenclamide-induced response (about 150%), EC$_{50}$ value being in this case close to 5 µmol·L$^{-1}$.

Example 4

Effect of Urolithin A, B, C or D Determined in INS-1 Insulin Secreting β-Cells in the Presence of Exendin (FIGS. 4A-D)

Exendin, a GLP-1 analog used for the treatment of diabetes, stimulates insulin secretion under high- but not low-glucose condition. Therefore, experiments were conducted in the presence of 8.3 mmol·L$^{-1}$ glucose and 0.001 µmol·L$^{-1}$ exendin.

Material and methods were the same as described in example 1. For the determination of insulin secretion, cells were incubated for 1h (5% $CO_2$, 37° C.) in KRB medium containing 8.3 mmol·L$^{-1}$ glucose (glucose-stimulated condition) and exendin (0.001 µmol·L$^{-1}$) in the presence or absence of the compounds tested. Data were expressed as percent of exendin (0.001 µmol·L$^{-1}$)+glucose (8.3 mmol·L$^{-1}$)-stimulated insulin secretion ("control 100%") (FIGS. 4A-D).

Figure 4A:
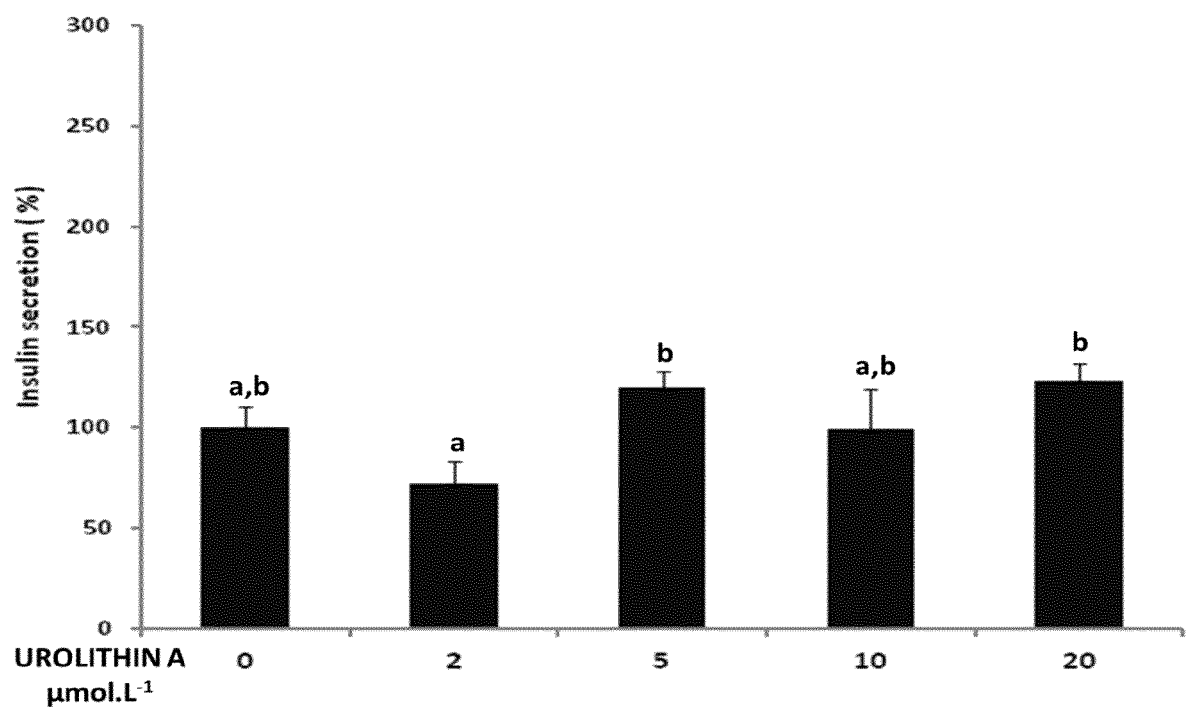
Figure 4B:
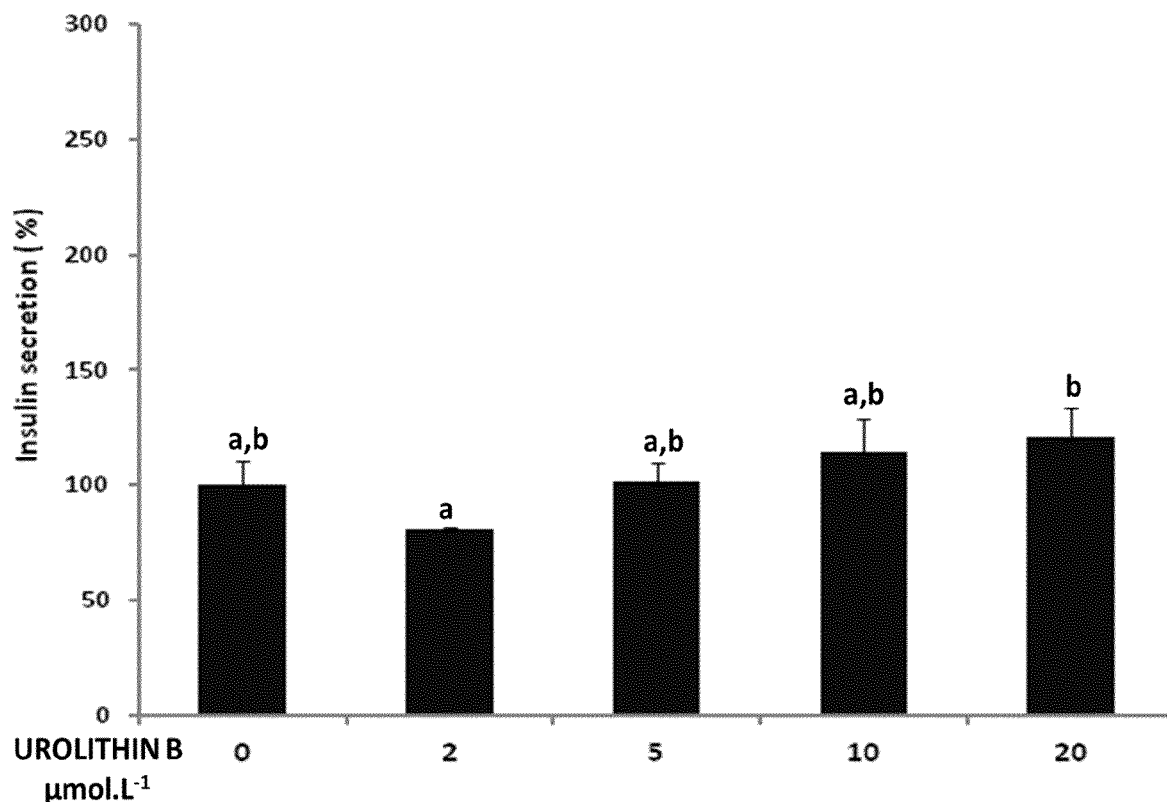
Figure 4C:
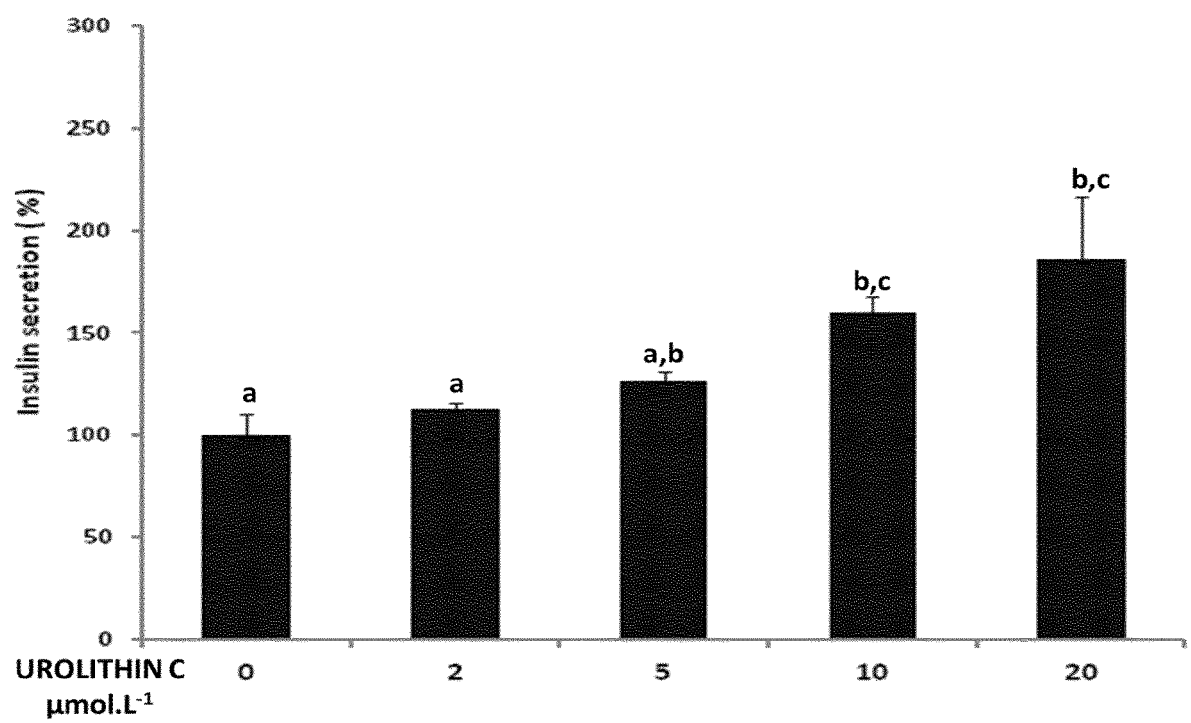
Figure 4D:
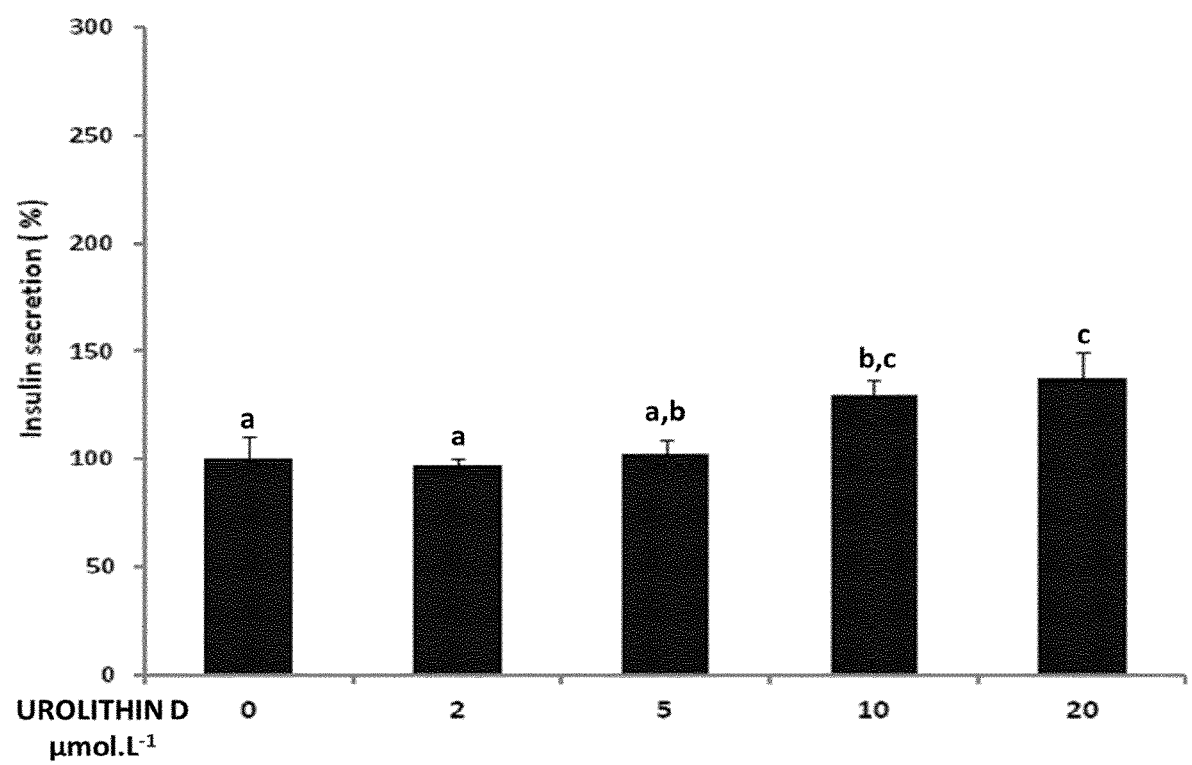
Figure 5A:
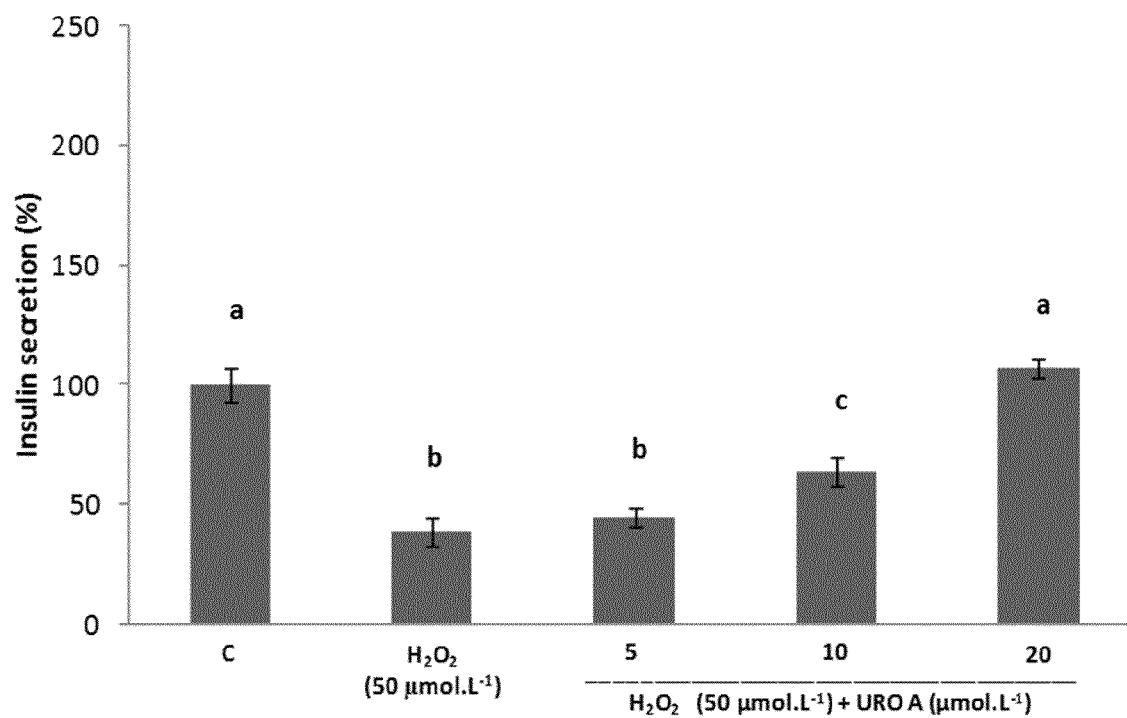
Figure 5B:
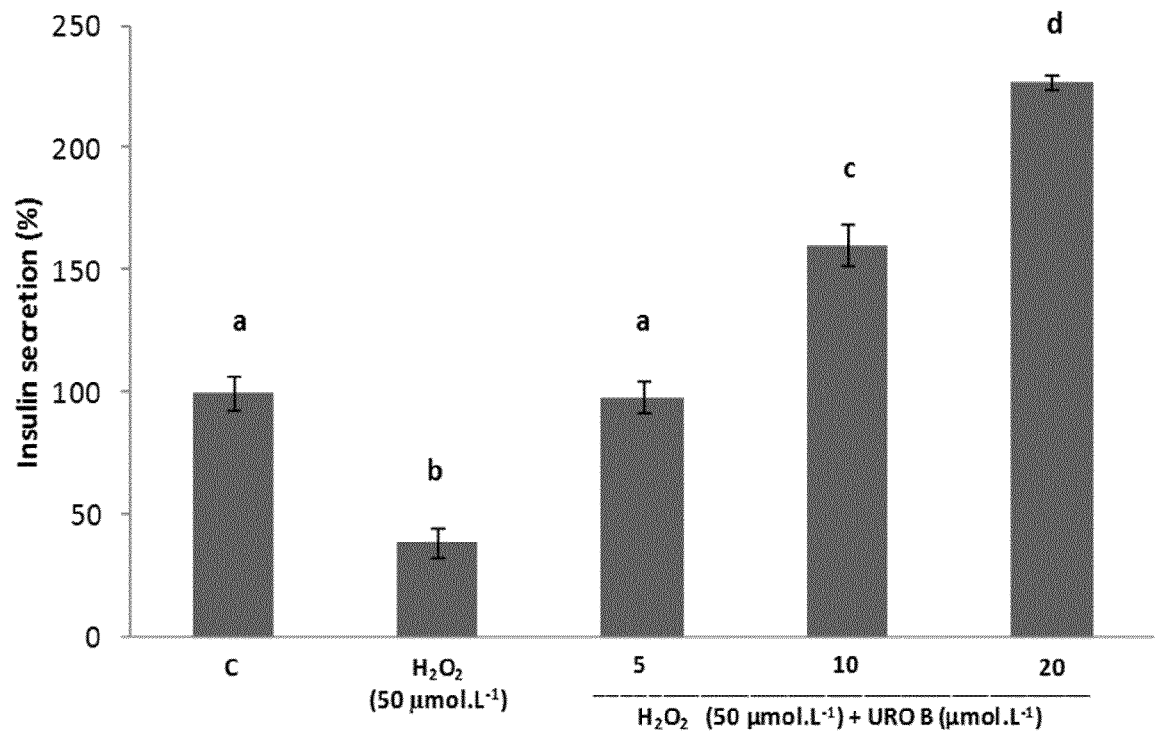
Figure 5C:
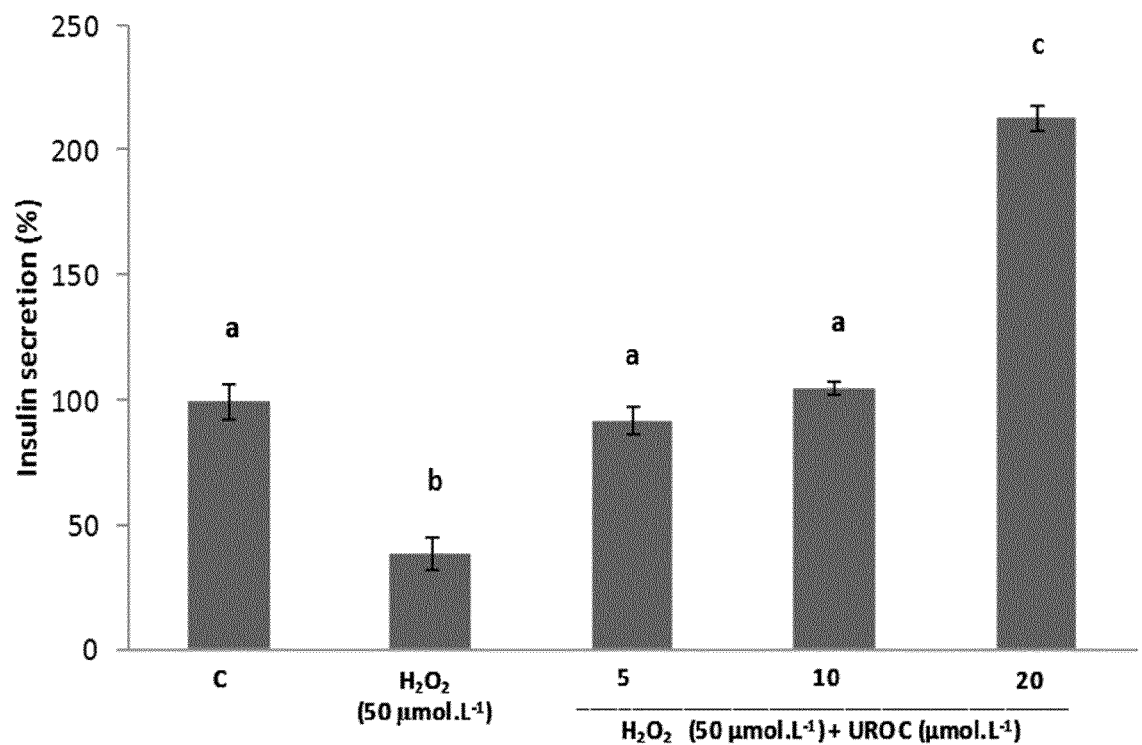
Figure 5D:
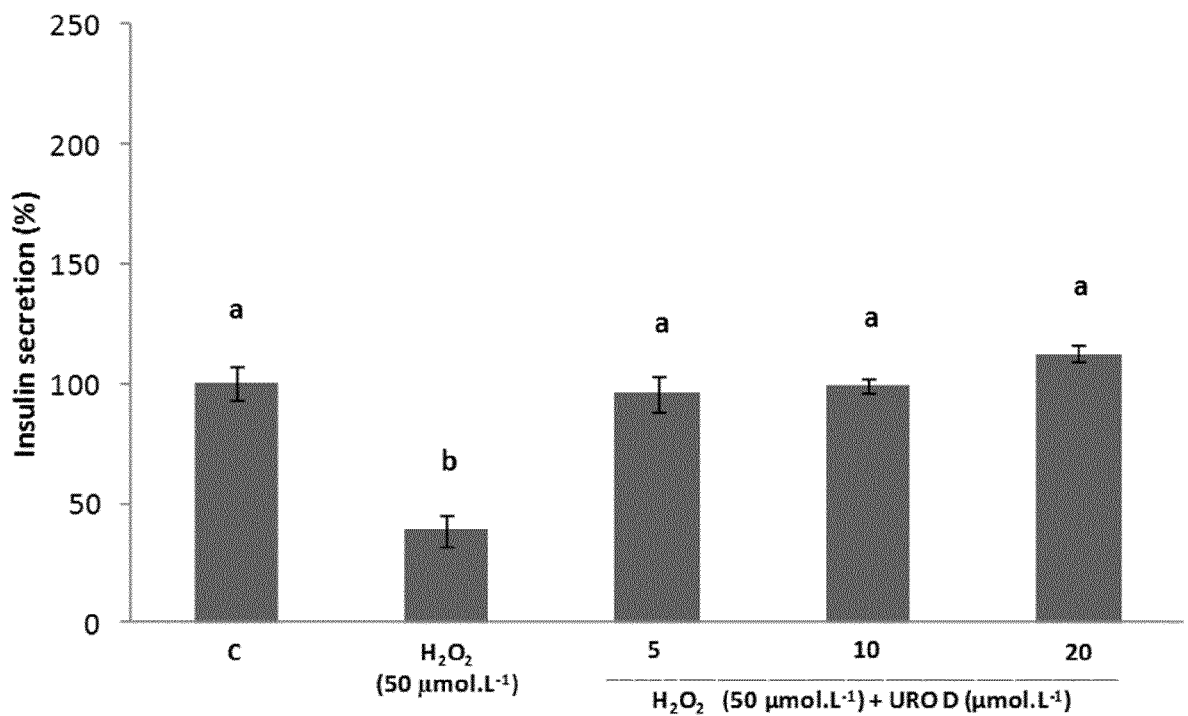

Results:

In the presence of exendin and glucose, the addition of urolithins A or B did not induce a significant raise of insulin secretion, as shown in FIGS. 4A and B. As opposed to urolithin A and B, the addition of urolithin C or D induced a significant concentration-dependent stimulation of insulin secretion, as illustrated in FIGS. 4C and 4D. Regarding maximal response, urolithin C appeared as the most active compound (about 185% stimulation as compared to exendin alone), while urolithin D induced a 140% stimulation.

Regarding active concentrations, maximal effects were obtained in both cases at the maximal concentration tested (20 µmol·L$^{-1}$). EC$_{50}$'s from both compounds could be estimated between 5 and 10 µmol·L$^{-1}$.

Example 5

Evaluation of the Protecting Effects of Urolithins Against Oxidative Stress in INS-1 Insulin Secreting β-cells (FIGS. 5A-D and 6)

As previously stated, one of the mechanisms potentially involved in the prevention of diabetes could be the protection of β-cells from insults induced by inflammation and oxidative stress (Bonora, 2008).

As oxidative stress is able to impair both β-cells insulin secretion capacity and viability (Kaneto et al., 1999), it is important to determine on insulin secretion and viability the effects of compounds potentially able to prevent or delay the evolution of diabetes.

It has been previously shown (Youl et al., 2010) that quercetin, but not resveratrol nor the anti-oxidant N-acetyl cysteine, was able to prevent $H_2O_2$-induced insulin secretion impairment. The possible protective effect of urolithins A-D under was therefore examined under the same experimental conditions. Insulin secretion was determined as previously described by measuring insulin accumulation after a one-hour incubation period and viability determined from the MTT test, an indicator of mitochondrial function.

Material and Methods:

a-INS-1 treatment

For protection experiments, INS-1 cells were pre-incubated with the indicated concentrations of urolithins for one hour (5% $CO_2$, 37° C.) in RPMI medium. After two washes in HEPES-balanced Krebs-Ringer bicarbonate buffer (123 mmol·L$^{-1}$ NaCl, 5.4 mmol·L$^{-1}$ KCl, 1.3 mmol·L$^{-1}$ KH$_2$PO$_4$, 2.7 mmol·L$^{-1}$ MgSO4, 2.9 mmol·L$^{-1}$ CaCl$_2$, 5 mmol·L$^{-1}$ NaHCO$_3$ and 20 mmol·L$^{-1}$ HEPES, pH 7.5) containing 2 g·L$^{-1}$ bovine serum albumin (KRB/BSA), INS-1 cells were incubated for one hour (5% $CO_2$, 37° C.) in KRB/BSA containing urolithins at the indicated concentrations in the presence of 1.4 mmol·L$^{-1}$ glucose (basal condition) or 8.3 mmol·L$^{-1}$ glucose (stimulant condition). When used, $H_2O_2$ (50 µmol·L$^{-1}$) was added at the beginning of the one-hour incubation period. Control experiments were performed in the basal condition, in the absence of urolithins during the pre-incubation and incubation periods.

b-Determination of insulin secretion

Insulin secretion was determined as described above by measuring insulin accumulation after a one-hour incubation period.

c-Determination of INS-1 cells viability:

Cell viability was determined using the 3-(4,5-Dimethylthiazol-2-yl)-2,5-diphenyltetrazolium bromide (MTT) assay. At the end of the one-hour incubation period, cells were washed with KRB/BSA and KRB/BSA containing 5 mg/ml MTT was added to each well. Plates were then incubated for 3 h in the dark in a humidified atmosphere (5%

$CO_2$, 37° C.). Cells were washed with phosphate buffered saline (PBS) and precipitates were dissolved in 50 μl dimethyl sulfoxide (DMSO). Absorbance of the reduced intracellular formazan product was read at 492 nm on a microtiter plate reader (Tecan, Lyon, France). Experiments were performed in quadruplicate.

Results:

The effects of Urolithins A-D on insulin secretion in the presence of oxidative stress are illustrated on FIGS. 5A-D.

As expected, $H_2O_2$ induced a major reduction of the degree of stimulation of insulin secretion by 8.3 mmol·$L^{-1}$ glucose.

All urolithins were able to prevent insulin secretion impairment induced by $H_2O_2$. However urolithins B, C and D were active for a concentration as low as 5 μmol·$L^{-1}$ while urolithin A was active for 20 μmol·$L^{-1}$ only.

In addition, Uro B (10 μmol·$L^{-1}$) was able to induce a 150% stimulation, while Uro B and C (20 μmol·$L^{-1}$) were both able to induce a 200% insulin secretion stimulation as compared to control conditions.

The effects of Urolithins A-D on cell viability are illustrated on FIG. 6.

As expected, $H_2O_2$ induced a major reduction in cell viability as determined from the MTT test (mitochondrial function).

As shown, Uro C and D were both able to totally prevent viability impairment while Uro B was partially active and Uro A had no effect.

In summary, Uro B -and at a lower degree Uro C-possess a particular effect of insulin secretion protection, while Uro C and D -and at lower degree Uro B- are active in preventing impairment of viability.

Due to structural similarities between urolithin C and isourolithin A (FIG. 1), a similar effect is expected for both urolithin C and isourolithin A.

Example 6

Effect of Urolithins A, B, C or D on Insulin Secretion Determined on a Physiologically Relevant Model, the Rat Isolated Pancreas Preparation (FIGS. 7A-B).

The isolated pancreas preparation is a model reproducing the in vivo situation, as pancreas is surgically extract and perfused through its normal circulation. Therefore, islets of Langherans and insulin secreting β-cells are exposed to compounds modulating insulin secretion through the normal circulation (arteries, capillaries and veins). It is the most physiologically relevant and predictive model for the determination of the effects and physiologically active concentrations of compounds on insulin secretion.

Material and methods:

Pancreas was isolated from male Wistar rats of 250-300 g body weight under pentobarbital anaesthesia (60 mg/kg i.p.). Previously described technique (Cadène et al., 1996) was used to isolate the pancreas from neighboring tissues. The organ was then transferred into a plastic chamber maintained at 37.5° C. Perfusion medium was Krebs-Ringer bicarbonate buffer containing 2 g/l bovine serum albumin and 5 mmol·$L^{-1}$ (non stimulant condition) or 8.3 mmol·$L^{-1}$ (stimulant condition) glucose, and continuously bubbled with a mixture of 95% $O_2$/ 5% $CO_2$. Infusion pressure was selected to provide a pancreatic outflow of 2.5 ml/min. The first sample was taken 30 min after initiation of perfusion to allow for an adaptation period. Two additional control samples were collected 10 and 15 min later, immediately followed by switching to the same buffer containing urolithins (10 μmol·$L^{-1}$). Pancreatic effluents were then collected at the following times (minutes): 17, 18, 19, 20, 21, 27, 32, 42. Pancreas was then washed using the same buffer in the absence of urolithin. Two additional samples were taken 5 and 15 min after urolithin withdrawal.

All samples were collected for 1 min allowing determinations of pancreatic effluent output, and immediately frozen for insulin assay (Cisbio HTRF method). Insulin output rate (ng/min) was calculated by multiplying the hormone concentration (ng/ml) in the effluent by the corresponding flow rate (ml/min).

Amplitude of stimulation of insulin secretion by urolithins was estimated by calculating the Area Under the Curve (AUC) of insulin produced above the basal level (trapezoidal rule). Before administration of urolithins, insulin secretion levels were 3.39±0.58 ng/min (n=14 pancreases) and 67.5±7.80 ng/min (n=15 pancreases), for 5 mmol·$L^{-1}$ and 8.3 mmol·$L^{-1}$ glucose, respectively.

Results:

Urolithins (10 μM) were all able to induce insulin secretion (change in basal insulin secretion rate), with some differences in their potencies, though. The corresponding AUC (ng insulin secreted for 32 min) were as follows:
urolithin A : 2609.5
urolithin B: 142.0
urolithin C: 9160.0
urolithin D: 387.5

In accordance with insulin secretion data obtained in insulin secreting INS-1 β-cells, urolithin C appeared as the most active compound, followed by urolithins A, D and B.

FIG. 7A-B illustrates the insulin secreting response to urolithin C obtained either under 8.3 mmol·$L^{-1}$ stimulating glucose condition (7A) or 5 mmol·$L^{-1}$ non-stimulating glucose condition (7B). As illustrated, urolithin C induced a major amplification under stimulating glucose condition and had no effect under non-stimulating glucose condition.

In addition, we found that urolithin C was able to induce some stimulation of insulin secretion for a concentration as low as 1 μM (not illustrated) in stimulating glucose condition but not in non-stimulating glucose condition.

These results validate on a physiologically relevant model reproducing the in vivo situation the potential use of urolithins as glucose-dependent insulin-secreting compounds. They also suggest that insulin-secreting activity will not occur under normo-glycemic conditions in vivo, reducing the risk of hypoglycemia, a common side-effect of insulin secretion stimulants (e.g. sulfonylureas) that stimulate insulin secretion even under normo-glycemic conditions.

This is an important feature for the development of urolithins for the prevention of the treatment of type 2 diabetes.

CONCLUSION

Insulin secretion regulatory effects of urolithins were first studied on INS-1 insulin-secreting β-cells under low-glucose or glucose-, glibenclamide- and exendin-stimulated insulin secretion conditions.

Urolithins stimulated insulin secretion in various experimental conditions at the maximal concentration tested (20 μmol·$L^{-1}$), with the notable exceptions of:
  urolithin A, which did not stimulate insulin secretion under low-glucose condition.
  urolithins A and B, which did not amplify exendin-stimulated insulin secretion.

These exceptions may indicate some different cellular mechanism between urolithins.

Noticeably, the degree of stimulation of insulin secretion by urolithins appeared similar between the different insulin secretion conditions: about 160% for urolithin A, 140% for urolithin B, 185-200% for urolithin C and 135-155% for urolithin D, suggesting that urolithin C was the most active compound (C>A>B≈D) Urolithin-induced stimulation does occur either under high or low level of insulin secretion conditions and in the presence of glucose and/or insulin secretion stimulating agents, suggesting that urolithins act as amplifiers of insulin secretion stimulants.

The potential of urolithins to protect β-cells against oxidative stress were also studied on the INS-1 β-cells both on insulin secretion and viability, knowing that quercetin- but not resveratrol or the antioxidant N-acetyl cystein- was previously shown to fully prevent viability and insulin secretion impaired by oxidative stress (Youl et al., 2010). Results (FIGS. 5 and 6) indicate that the various urolithins do possess differential capacities to protect cells against the oxidative stress-induced impairments of insulin secretion (notably urolithin B and C) or viability (notably urolithins C and D).

The effects of urolithins on insulin secretion were also determined on a physiologically relevant model, the rat isolated perfused pancreas.

On this model, urolithins (10 μM) were able to amplify insulin secretion in a 8.3 mmol·L$^{-1}$ stimulating glucose condition, but not under a 5 mmol·L$^{-1}$ non-stimulating glucose condition. Order of potencies of urolithins to amplify insulin secretion in this model appeared as C>>A>D>B, in good agreement with data obtained on INS-1 β-cells. Again, urolithin C appeared as the most active compound and some response was obtained for a concentration as low as 1 μM. Also, our results suggest that the effects of urolithins are glucose-dependent and, as opposed to sulfonylureas, may not induce hypoglycemia when exposed to normo-glycemic conditions.

In summary, our data suggest that urolithins act as amplifiers of physiological (glucose)-or drug-induced insulin secretion, their $EC_{50}$'s being around 5 to 10 μmol·L$^{-1}$.

In summary, urolithin C seems to be the most active compound as a glucose-dependent stimulant of insulin secretion, although other urolithins may display additional protective effects on β-cells.

BIBLIOGRAPHIC REFERENCES

Bardy et al., *Br J Pharmacol.* 2013, 169:1102-13.
Bialonska et al., *J. Agric. Food Chem.* 2009, 57: 10181-10186.
Bonora, *Nutr. Metab. Cardiovasc. Dis.* 2008,18: 74-83
Cadène A et al., *Eur J Pharmacol.* 1996, 318:145-51.
Cerda et al., *Eur. J Nutr.* 2004, 43: 205-20.
Cerda et al., *J Agric Food Chem.* 2005, 53:5571-6.
Del Rio et al., *Antioxid Redox Signal.* 2013, 18: 1818-1892.
Kaneto et al., *Diabetes.* 1999, 48: 2398-406.
Garber, *Diabetes, Obesity and Metabolism.* 2012, 14: 399-408.
González-Sarrías et al., *J Agric Food Chem.* 2013, 61:4352-9.
Li et al., *Biochem Soc Trans* 2008, 36: 930-934
Lucas et al., *Carbohydr. Res.* 2009, 344:1340-1346.
Palsamy and Subramanian, *Biomed Pharmacother.* 2008, 62: 598-605.
Pinto et al., *J Med Food.* 2010, 13:1027-35.
Poitout and Robertson, *Endocr Rev* 2008, 29: 351-366.
Tulipani et al., *J Agric Food Chem.* 2012, 60: 8930-40.
Youl et al., *Br J Pharmacol.* 2010, 161: 799-814.

The invention claimed is:

1. A method for treating type 2 diabetes comprising administering, to a mammal in need thereof, urolithin C, and a compound able to stimulate insulin secretion, wherein said compound able to stimulate insulin secretion is selected from the group of: sulfonylureas, GLP-1 analogs, and DPP4 inhibitors.

2. The method according to claim 1, wherein the compound able to stimulate insulin secretion is a sulfonylurea that is glibenclamide.

3. The method according to claim 1, wherein the compound able to stimulate insulin secretion is a GLP-1 analog that is exenatide.

* * * * *